US010342431B2

(12) United States Patent
Drugge

(10) Patent No.: US 10,342,431 B2
(45) Date of Patent: *Jul. 9, 2019

(54) METHOD FOR TOTAL IMMERSION PHOTOGRAPHY

(75) Inventor: Rhett Drugge, Stamford, CT (US)

(73) Assignee: MELANOSCAN LLC, Stamford, CT (US)

( * ) Notice: Subject to any disclaimer, the term of this patent is extended or adjusted under 35 U.S.C. 154(b) by 149 days.

This patent is subject to a terminal disclaimer.

(21) Appl. No.: 12/102,810

(22) Filed: Apr. 14, 2008

(65) Prior Publication Data

US 2008/0194968 A1 Aug. 14, 2008

Related U.S. Application Data

(62) Division of application No. 09/625,712, filed on Jul. 26, 2000, now Pat. No. 7,359,748.

(51) Int. Cl.
*A61B 5/00* (2006.01)
*A61B 5/15* (2006.01)

(52) U.S. Cl.
CPC .......... *A61B 5/0064* (2013.01); *A61B 5/0071* (2013.01); *A61B 5/1444* (2013.01);
(Continued)

(58) Field of Classification Search
USPC ....... 600/476, 407, 477, 478, 479, 480, 587, 600/473; 250/317.1–345; 700/90;
(Continued)

(56) References Cited

U.S. PATENT DOCUMENTS 5,261,404 A 11/1993 Mick et al.
5,692,511 A * 12/1997 Grable ................ A61B 5/4312
250/330
(Continued)

FOREIGN PATENT DOCUMENTS

AU 2891400 A 7/2000
GB 2328280 A 2/1999
(Continued)

OTHER PUBLICATIONS

Hurley, J., Demers, M., Wulpern, R., Grindon, J., "Body Measurement System using White Light Projected Patterns for Made-to-Measure Apparel," Proc. SPIE 3131, Optical Scanning Systems: Design and Applications, Jul. 7, 1997, pp. 212-223.
(Continued)

*Primary Examiner* — Rochelle D Turchen
(74) *Attorney, Agent, or Firm* — McCarter & English, LLP

(57) ABSTRACT

Total Immersion Photography (TIP) is disclosed, preferably for the use of screening for various medical and cosmetic conditions. TIP, in a preferred embodiment, comprises an enclosed structure that may be sized in accordance with an entire person, or individual body parts. Disposed therein are a plurality of imaging means which may gather a variety of information, e.g., chemical, light, temperature, etc. In a preferred embodiment, a computer and plurality of USB hubs are used to remotely operate and control digital cameras. The photo information is then transferred via the USB to the computer for processing and aggregation. Subject information is gathered to configure the operation of the various parameters of the device.

38 Claims, 5 Drawing Sheets

(52) U.S. Cl.
CPC .............. *A61B 5/411* (2013.01); *A61B 5/415* (2013.01); *A61B 5/418* (2013.01); *A61B 5/442* (2013.01); *A61B 5/445* (2013.01)

(58) Field of Classification Search
USPC ........................................................ 332/117
See application file for complete search history.

(56) References Cited

U.S. PATENT DOCUMENTS

| | | | |
|---|---|---|---|
| 5,782,762 | A | 7/1998 | Vining |
| 5,797,845 | A | 8/1998 | Barabash et al. |
| 5,850,289 | A | 12/1998 | Fowler et al. |
| 5,853,370 | A * | 12/1998 | Chance et al. ............... 600/473 |
| 5,865,829 | A | 2/1999 | Kitajima |
| 5,879,306 | A | 3/1999 | Fontenot et al. |
| 6,011,986 | A | 1/2000 | Diab et al. |
| 6,083,162 | A | 7/2000 | Vining |
| 6,236,875 | B1 | 5/2001 | Bucholz et al. |
| 6,272,367 | B1 * | 8/2001 | Chance .......................... 600/407 |
| 6,289,107 | B1 * | 9/2001 | Borchers ................. A43D 1/02 356/391 |
| 6,301,549 | B1 * | 10/2001 | Barney .......................... 702/167 |
| 6,339,216 | B1 | 1/2002 | Wake |
| 6,373,963 | B1 | 4/2002 | Demers et al. |
| 6,397,091 | B2 | 5/2002 | Diab et al. |
| 6,546,356 | B1 * | 4/2003 | Genest .......................... 702/153 |
| 6,556,858 | B1 | 4/2003 | Zeman |
| 6,597,941 | B2 | 7/2003 | Fontenot et al. |
| 6,907,138 | B1 * | 6/2005 | Hoffman ................. G01B 11/30 382/154 |
| 6,993,167 | B1 * | 1/2006 | Skladnev ............. A61B 5/0059 382/128 |
| 7,092,014 | B1 | 8/2006 | Li et al. |
| 2004/0092827 | A1 * | 5/2004 | Zavislan et al. .............. 600/476 |

FOREIGN PATENT DOCUMENTS

| | | |
|---|---|---|
| GB | 2337390 A | 11/1999 |
| GB | 2346494 A | 8/2000 |
| GB | 2350511 A | 11/2000 |
| GB | 2352901 A | 2/2001 |
| GB | 2355612 A | 4/2001 |
| GB | 2355789 A | 5/2001 |
| GB | 2358752 A | 8/2001 |
| GB | 2364494 A | 1/2002 |
| WO | 9828908 A1 | 7/1998 |
| WO | 9956249 A1 | 4/1999 |
| WO | 9960525 A | 11/1999 |

OTHER PUBLICATIONS

Whitestone,J., Files, P., Burnsides, D., "Integrate 1.25: A prototype for evaluating three-dimensional visualization, analysis and manipulation functionality", CARD-lab., Wright Patterson Air Force Base, OH, May 1996, 140 pages.

Jones, P., West, G., Harris, D., Read, J., "The Loughborough anthropometric shadow scanner (LASS)," Endeavour, New Series, vol. 13, No. 4, 1989, 7 pages.

Blair, A., "Mass Customization Seeking Mass Appeal", Daily News Record, Accessed Dec. 27, 2017 at https://www.highbeam.com/doc/1G1-55287453.html/print, Jul. 19, 1999, 3 pages.

Micrographics and Hybrid Imaging Systems Newsletter, "Wicks and Wilson Limited.(Brief Article)", Accessed Dec. 27, 2017 at https://www.highbeam.com/doc/1G1-57102937.html/print, Sep. 1, 1999, 1 page.

Braggins, D. "3-D Human Image Capture in Europe: Maturing", Accessed Dec. 27, 2017 at https://www.highbeam.com/doc/1G1-64161368.html/print, Jul. 1, 2000, 4 pages.

Computergram International, "Tricorder to Raise More Capital for 3D Technology", Accessed Dec. 27, 2017 at https://www.highbeam.com/doc/1G1-53594917.html/print, Jan. 19, 1999, 1 page.

Cyberware, "Cyberware Whole Human Scanning", website printout from https://web.archive.org/web/19970503064824/http://www.cyberware.com:80/products/wholebody_datasheet.html, Oct. 22, 1996, 2 pages.

Douros, I., Dekker, L., Bernard, B., "Reconstruction of the surface of the human body from 3D scanner data using B-splines", Proc. SPIE 3640, Three-Dimensional Image Capture and Applications II, Mar. 8, 1999, 12 pages.

Bowser, A., "Total Body Imaging the 'Way to Go,' Internet Head Says", Dermatology Times, vol. 20 Issue 5, p. 48, May 1999, 2 pages.

Demers et al., "Three-dimensional surface capture for body measurement using projected sinusoidal patterns," Procedures of SPIE 3023, Three-Dimensional Image Capture, Jul. 7, 1997, 14 pages.

Voigt, Fl, Classen, R., "Topodermatographic Image Analysis for Melanoma Screening and the Quantitative Assessment of Tumor Dimension Parameters of the Skin," Cancer, vol. 75, No. 4, Feb. 15, 1995, pp. 981-988.

Daanen, H., van de Water, J., "Whole Body Scanners," Displays 19 (1998), Mar. 2, 1998, pp. 111-120.

Daanen, H., "3-D Surface Anthropometry: accurate determination of body dimensions", NATO Panel 8 RSG 24 Workshop on Emerging Technologies in Human Engineering and Testing & Evaluation, Jun. 24-26, 1997, seven pages.

Newton, I. and Mitchell, H.L., "Medical Photogrammetry," Chapter 11 in "Close Range Photogrammetry and Machine Vision" (Atkinson, ed.), Whittles Publishing, 1996, pp. 303-327.

Deacon, A.T., Anthony, A.G., Bhatia, S.N., & Muller J.-P., "Evaluation of a CCD-based Facial Measurement System," Medical Informatics, vol. 16, No. 2, 1991, pp. 213-228.

Comer, R., et al., "Talking Digital", Photogrammetric Engineering & Remote Sensing, Dec. 1998, pp. 1139-1142.

Manual of Photogrammetry, published by the American Society of Photogrammetry, 4th Edition, 1980, pp. 801-809.

"USB powers up for market thrust," Office World News, Sep. 1, 1998, three pages.

"What's the big deal about USB," Info-Tech Advisor Newsletter, Jan. 12, 1999, two pages.

* cited by examiner

METHOD FOR TOTAL IMMERSION PHOTOGRAPHY

CROSS-REFERENCE TO PRIORITY APPLICATION

This patent application is a divisional of U.S. patent application Ser. No. 09/625,712, filed Jul. 26, 2000, entitled "APPARATUS FOR TOTAL IMMERSION PHOTOGRAPHY," co-pending herewith, which is hereby expressly incorporated by reference as part of the present disclosure.

FIELD OF THE INVENTION

The present invention relates primarily to conditions pertaining to health and cosmetics. As such, the device allows for the imaging of total or subtotal non-occluded body surfaces in order to detect health and cosmetic conditions and involves the measurement and analysis of an optically depicted image of a patient's surfaces by standard color imaging, heat, electromagnetic or chemical imaging. The present invention allows for image pixel acquisition, its data collection, data aggregation, data dissemination, data manipulation, and subsequent viewing. The present invention provides for tissue analysis of a patient such that relevant determinations may be made such as detection of diseases or related problems of cosmesis.

BACKGROUND OF THE INVENTION

The invention relates to the detection, diagnosis and treatment of skin cancer as well as other diseases and cosmetic conditions of the visible human.

Half of all new cancers are skin cancers. About 1.3 million new cases of skin cancer will be diagnosed in the United States each year. About 80 percent of the new skin cancer cases will be basal cell carcinoma, 16 percent are squamous cell carcinoma, and 4 percent are melanoma.

Both basal cell carcinoma and squamous cell carcinoma have a better than 95 percent cure rate if detected and treated early. Squamous cell carcinoma of the skin accounts for about 2.3 thousand deaths annually.

The incidence of melanoma has more than tripled among Caucasians between 1980 and 2000. There will be about 47,700 new cases of melanoma in 2000. At current rates, one in 74 Caucasian Americans will develop melanoma. With that statistic, one person dies of melanoma every hour. This year, approximately 7,700 deaths will be attributed to melanoma in the ratio of 4,800 men and 2,900 women. Older Caucasian males have the highest mortality rates from melanoma. In women under the age of 30, melanoma is more prevalent than breast cancer. All of these cancers are associated with sun exposure with the majority occurring after age 50. Furthermore, the incidence rates for all skin cancers are increasing with movement of white populations south to sunnier climates and the greater numbers of individuals living into their 80s. With the "baby boomer" generation currently in their late 50s, the medical community is faced with an explosive skin cancer epidemic.

There is a need for a practical device that allows for the rapid screening of individuals for skin cancer and other maladies of the skin in early stages of development.

Currently, clinical diagnosis of skin disease is generally accomplished by visual inspection under white light illumination. In this process, the reflectance light of a skin lesion is examined. Visual diagnosis alone may not be particularly accurate for early detection of skin cancer since many skin conditions have a similar appearance under white light. Therefore, when a suspect lesion is identified by visual examination, a biopsy is often performed for a definitive diagnosis. Not only is it crucial to diagnose skin pre-cancer or skin cancer at an early stage when it is curable, but it is also important to improve the clinical diagnosis of suspected skin lesions so as to avoid unnecessary skin biopsies.

Several approaches have been tried to improve skin cancer diagnosis. Digital processing of reflectance images has been extensively investigated recently and has been found in melanoma to be more accurate than specialist diagnostic accuracy. An alternative approach is ultraviolet (UV), infrared (IR) or polarized light photography that extends visual perception of a physician to the UV, IR or polarized light reflectance patterns. A further alternative approach that is already in widespread medical use involves illuminating the skin with a "Wood's lamp" which consists of a mercury discharge lamp associated with a filter that transmits UVA light with a 365 nanometer peak while absorbing visible light. When this device is used to assist in skin diagnosis, the eye serves as both the detector and the long pass filter. The eye is not sensitive to UV light, but is sensitive to visible fluorescence light. When the "Wood's lamp" is used in a darkened room, where the physician sees an image of a fluorescing disease site. The "Wood's lamp" is useful for the diagnosis of some skin conditions such as tinea capitis, tinea versicolor, erythrasma, and some pseudomonas infections, as well as aiding in the detection and diagnosis of hypopigmented skin. It is of no value in conditions where the fluorescence is not in the visible spectrum. These techniques depend on lighting and sensor techniques and may be incorporated into the total immersion photography system.

Prior Disclosures

Currently, clinical diagnosis of skin disease is generally accomplished by visual, verbal and handwritten history taking and by inspection during a visit to the physician's clinic. Initial inspections are routinely performed by general practitioners. Dermatologists may be sought out by patients or used upon referral by general practitioners. Either way, an appointment is required. Visual inspections are often limited by the physician's schedule or patient modesty. The patient may only be willing to have the area of concern inspected. General practitioners, the HMO "gatekeepers", have been documented to be less effective in discerning potential cancerous lesions than dermatologists. If referrals are not made, possible malignancies may be overlooked. A second approach is chemical emulsion or digital photography that can extend visual perception of a physician to the UV or IR reflectance patterns. Such approaches have also been limited by the need for a "point-and-shoot" photographer. A more limited approach requires only images of those areas in question. This again leaves open the possibility of an incomplete diagnosis. This approach may be augmented by the use of skin surface epiluminescence microscopy. Epiluminescence light microscopy (ELM) represents a technique which permits examination of the surface of the skin and also—by using the oil immersion technique—of the dermal-epidermal junction zone. The commonly used method of epiluminescence microscopy is based on point and shoot techniques requiring a trained operator. Recently, there have been investigations into the use of digital imagery to aid with dermatologic diagnoses. The prevalent technique uses either digitally processed standard photography or direct digital photography of sections of the subject's body. These images are then stored for inspection, referral, and/or forwarding. For comprehensive surface imaging, this approach requires multiple posings by the photographer and the subject that may exceed 30 views in total. Depending on the medium used, review of the images may or may not be available for inspection during the same appointment. Specific applications include the MoleMap and MoleMax II systems. MoleMap uses a combination of three images (epiluminescence, macro and low resolution) to identify possible melanoma. Visual type resolution is used primarily for mapping suspicious locations. Images are diagnosed and reported on by dermatologists before being permanently archived on a computer system for future comparisons. The MoleMax II system combines epiluminescence microscopy and computer technology for data storage and retrieval. The system can be adapted for body surface imaging (using serial individually-photographed images). Images are available for inspection during the current office visit, allowing simultaneous dermatologist/patient on-screen observation. Since the outcome of treatment of cancer is more favorable the earlier and more accurately the cancer is detected, the present invention is a substantial advancement in improving public health by eliminating the barrier of an available expert photographer or dermatologist for effective skin screening. This device provides a complete non-covered screening in an automated fashion, removing the intrusion of physical inspection and decreasing the possibility of missed lesions. The image acquisition does not require the presence of a physician or medical photographer, thereby increasing convenience to the patient/subject. This, in turn, would allow the placement of the device independent of the physician's or medical photographer's office, a benefit to public health programs.

Since the outcome of cancer treatment is more favorable the earlier and more accurately the cancer is detected, the present invention is a substantial advancement in improving public health by automating the imaging of potentially cancerous lesions in a more rapid and complete method. In light of the many advantages of early detection, there exists a clear need for a device that can greatly enhance the current methods of skin cancer screening. Furthermore, such a device will also find use in the cosmetic and beauty industry.

SUMMARY OF THE INVENTION

The TIP system including the structure, infrastructure, and imaging system, requires little training, minimal staffing, and may be constructed with simple, easily available tools. TIP is a device that may be easily transportable, providing opportunity for skin screenings in diverse locations such as gym facilities, recreation centers, physician's offices, and other health oriented facilities. Medically under-served and restricted locales, e.g., rural areas and prison facilities, will also benefit from TIP system remote diagnostic capabilities (telemedicine), bringing the care of medical specialists to the patients.

The present invention, Total Immersion Photography (TIP), relates initially, and thus generally, to cancer detection and, more particularly, to skin cancer, e.g., melanoma, detection involving the measurement and analysis of an optical depiction of the subject patient's skin surface by standard color imaging, as well as heat, electromagnetic or chemical imaging. The present invention allows for subject acquisition, data collation, data aggregation, data dissemination, data manipulation, data viewing in a preferable medium and analysis of a subject patient's skin surface, or other body tissue and, therefore, providing for the subject tissue's analysis such that relevant determinations may be made. TIP is a digital image acquisition device, the products of which, are capable of a variety of applications. For instance, panoramic mosaics of the body, 3-D models of the body, images for use with "machine vision", and interfacing with medical records are such possible uses.

The present invention is uniquely situated whereby TIP may operate as the screening test, as well as a confirmation of a positive result from a screening test, or even in a manner that provides for second opinions. In either circumstance, if the results of the administered test are confirmatory, i.e., melanoma is detected or otherwise identified on the skin surface. If, on the other hand, it is determined that melanoma is not present on the skin surface and, consequently, that the screening test was erroneous, the patient is spared the trauma of having to undergo the full work-up including the biopsy. In that respect, confirmation of cancer by analyzing the skin surface as set forth herein has many significant advantages over conventional melanoma tests, as well as cancer detection methods in general.

TIP comprises an image acquisition device that is further comprised of an enclosed structure that is and can be designed and assembled according to the human physiology to be analyzed such that the enclosed structure maximizes the ease of acquisition of the human body with traditional and/or digital photography. For purpose of discussion herein, the TIP structure may be comprised of fourteen (14) "panels". These fourteen (14) panels should be set forth in such that one panel has a "mirror image" panel. Alternatively, the TIP device may be constructed in a circular derivative, or like structure, of the fourteen (14) panel embodiment or other such number of panels keeping with the operative requirements of the device.

Contained within the enclosed structure are devices capable of "photographing" the body in a static position (motion or time-lapsed photography is also be provided for). The photographic device(s) may be capable of "taking" the body through traditional photography means, and/or temperature, chemical or electromagnetic based means. For purposes of discussion herein, the photographic means, e.g. a camera or like device capable of "capturing" a still image or video streamed images, ("camera") array should consist of no less than forty (40) cameras. The camera(s), as envisioned and discussed herein are set forth in the fourteen "panels" such that there are five (5) cameras per vertical panel section (8×5+ top and bottom cameras=42). This structure of cameras and panels may be easily modified without departing from that which is taught, disclosed and intended. The basis for the panel-camera array is to accurately capture the physiological attributes desired from the subject patient. With subject placement, the camera array coordinates and distances are known in relation to the subject. These distances, in combination with focal length and resolution information, allows for the precise measurement of the human features of interest. The camera(s) may be left "on", engaged or otherwise activated at a desired time.

To effect the proper "picture" lighting or other optical, heat, chemical or electromagnetic, enhancement means may be affixed to, or placed around the structure such that the photographic device's "capturing" of the subject physiology may be optimized. Accordingly, for purpose of discussion herein in regard to traditional photographic means the photographic optimization may be accomplished via a lighting means which consists of fluorescent lights. These lights should be situated and placed behind panels constructed of Lucite or like material containing the same or similar physical and optical properties. The lighting means may be "on" or activated prior to engagement of the camera or photographic means, or further, remotely triggered at a predetermined time.

In the event the camera(s) and/or the lighting means are triggered remotely or upon a sequencing event the same can be controlled manually or through computer assistance. Should computers or like devices be used to facilitate the process, the same may consist of at least one (1) USB Hub, but as is contemplated herein ten (10) USB Hubs with 7 (7) USB ports per hub. In turn, there should be a data processor or like means that resides on a server or so similarly situated.

The subject patient or physiological area would enter or be placed into the TIP enclosed structure, and if need be into the specified position for imaging. When in position, the camera device and enhancement, if not engaged, are so engaged and the image(s) obtained. Thereafter, the images are transmitted from the camera device(s) through the USB(s) onto a server/computer means capable of aggregating, manipulating and disseminating the image(s) collected into a visually discernable format. As such, the images can be displayed synchronously in 2D format or processed into 3D renderings for desired or required viewing.

As a result of the aforementioned TIP device, a doctor or other individual interested in acquiring the imaging of an individual or physiological area is provided a device capable of acquiring specific imagery and related information that may be further viewed, and/or collected, registered and/or stored for analysis. And as is considered and contemplated herein in regard to conditions and diseases of the visible human (but to also include and not limited to general physical, topical and subcutaneous analysis).

Accordingly, the apparatus of the present invention provides means for diagnosis of a skin disease site using spectral analysis comprising: a light source for generating light to illuminate the disease site; a probe means to conduct the illumination light from the light source to the disease site and to collect the reflected and fluorescence light and conduct said light to be analyzed; and spectral analysis means optically connected to the probe means for generating and displaying spectral measurements of the fluorescence light and the reflectance light to assist the user in diagnosing the disease site.

In a further aspect, the present invention provides a method for diagnosis of a skin disease site using spectral analysis comprising the steps of: illuminating the disease site with a light source to generate fluorescence and reflectance light at the disease site; collecting the generated fluorescence and reflectance light; conducting a spectral analysis of the collected light using a spectrometer; displaying spectral measurements of the fluorescence light and the reflectance light; and analyzing the measured fluorescence and reflectance spectra together to make a diagnosis of the disease site.

In a preferred embodiment, the apparatus of the present invention includes a compact spectrometer connected to a computer, a fluorescence excitation light source with a shutter, a white light source with a shutter, a bifurcated fibre bundle, a light coupler, a skin probe, and controlling electronics. The system is designed to automatically switch between the fluorescence excitation light and the white light sources and complete fluorescence and reflectance spectral measurements of a skin disease site sequentially in a few seconds. The system exploits the spectral differences of different skin diseases to aid in the dermatologic diagnosis. In particular, the apparatus provides a low cost, compact system that is capable of quickly and efficiently performing combined fluorescence and reflectance spectral analysis.

Applications

Below are some examples, but not limited to, in regard to the invention's scope and intended applications of TIP:

Automated Acquisition

Storage and display of the non-occluded visible body surface properties including but not limited to diseases and cosmetic conditions of the skin, hair and nails and body measurements. In this application the body surface can be viewed and measurements taken, evaluated, viewed, collated, and cross-referenced in an easy and efficient manner.

Melanoma and Skin Cancer Screening

Large populations can be effectively screened in a short period of time for skin cancers and related maladies using this device. The consistent lighting and repeatability of the imaging technique make it ideal for replacing the skin cancer screening environment where poor lighting, patient movement and dialogue, patient modesty and other factors increase the likelihood of an incomplete examination. By removing most of these factors, the physician is allowed undistracted viewing time of the patient's skin surface. In addition, the travel and time expense of skin cancer screenings at a location other than the physician's own office is large. For evaluations of change over time and detection of new lesions, 3-month, 6-month and yearly scans can be obtained and analyzed in relation to one another. All evaluations can be viewed, collated, and cross-referenced in an easy and efficient manner such that patient, doctor and health care provider time is minimized (and thus cost reduced). Data will be recorded and aggregated such that accurate assessments of the patient and population may be derived.

Medical Practice Aid/Documentation System

The availability of images of a patient undergoing therapy is critical to a practicing dermatologist who bases his/her clinical evaluation on the "improvement" he/she sees in the patient over time. This is especially pertinent to chronic conditions such as acne, urticaria, atopic dermatitis, contact dermatitis, psoriasis, blistering disorders, etc. The system acts as a "medical memory" of the patient as he/she returns to the office for reevaluation.

Beauty Evaluations

Consumers flock to cosmetic counters to purchase makeup to hide their skin conditions. Eighty percent of skin cancers are found on the head and neck. A "beauty mark" that is identified by the patient on the face could be dermatosis nigra, seborrheic keratosis, compound nevus or melanoma. A raised pink or red "pimple" could be a basal cell carcinoma or granuloma or sarcoid lesion. Other conditions include broken blood vessels (red lines) which can be indicative for diagnoses of telangectasias and rosacea. Pigment disorders such as vitiligo (lack of melanin), melasma (increased melanin), as well as discolorations due to excessive sun exposure are challenging to hide with makeup. Inflammatory skin conditions such as seborrheic dermatitis, psoriasis and eczema cause red, scaly patches which are chronic conditions falsely managed by moisturizers and makeup formulations. The information can be used to aid in makeover consultations. Consumers can be evaluated as to their current skin regimens and their conditions and followed over time as they undergo medical therapy. In addition, topical and internal medicines can be studied for their effectiveness over time.

Body Morphology Analysis-Shape Evaluation

Medically consequential conditions of the skeleton such as limb deformities and the spine deformities of kyphosis and scoliosis may be assessed photogrammetrically through TIP system. The consumer is also curious about what "shape" they are in mainly for appearance reasons. The physician or physical trainer is interested in the "shape" of the patient or client for both health and beauty reasons. This invention allows for a total body evaluation on several dimensions. Measurements and comparisons of body contours, fat deposit analysis, assymetry, etc. with volume measurements will be valuable for the cosmetic surgeon, the physician, the physical trainer, the clothier, etc. Medical and health decisions will be aided with such information. These evaluations can then be viewed, collated, and cross-referenced in an easy and efficient manner.

Cosmetic Surgery Applications

Preoperative evaluations as well as postoperative analysis and comparisons can be made using this device for all cosmetic surgery procedures. This is especially true for but not limited to facial surgery, eyelid surgery, face lifts, neck lifts, laser resurfacing, laser hair removal, soft tissue augmentation and liposuction. The physician can look to reduce asymmetry of the patient's anatomy to enhance the outcome of cosmetic surgery. In addition, measurements of graft survival and soft tissue survival as well as measurements of soft tissue removal can be more accurately defined. These evaluations can be viewed, collated, and cross-referenced in an easy and efficient manner such that studies can be made of the procedures where there are currently none.

Soft Tissue Manipulation

Volumetric measurements of soft tissue will facilitate studies of cosmetic procedures of the subcutis, glands, muscles, and skeleton. It will enhance the accuracy of body volume measurements for both soft tissue augmentation and soft tissue removal. Patients will be measured before soft tissue manipulation so that the procedure is more accurately applied to the areas to be treated. The volumetric data will serve as a baseline to study the effectiveness of the treatment and will also enhance postoperative evaluation. For soft tissue augmentation using live tissue, it will allow for survival studies to be conducted. This will be a significant improvement over the current water-displacement techniques and 2D renderings. These evaluations can be viewed, collated, and cross-referenced in an easy and efficient manner such that patient and doctor time is minimized. Data can be reviewed in a postoperative environment to assess outcomes and be used for outcome studies.

Percent of Surface Involved Score Calculation

This device will be able to standardize the Percent of Surface Involved ("POSI") and Psoriasis Area Surface Involvement ("PASI") scoring for the evaluation of extent of disease of such skin diseases but not limited to psoriasis, pemphigus, burn victims, etc. Automation of the calculation will be critical. Topical and internal medicines can be studied for their effectiveness over time. These calculations can be collated and cross-referenced in manner such outcome studies of therapies can be collected for large populations and published.

Hair Loss Evaluation

Progression of hair loss and treatment evaluation can be monitored with such a device. Topical and internal medicines can be studied for their effectiveness over time. In addition, hair transplantation techniques (planning, mapping and performing) will be enhanced. Postoperative and follow-up graft survival studies will also be more accurate. Such an evaluation procedure can be viewed by patient and health care professional alike, whereafter the same may be collated, and cross referenced in a manner such that time is minimized, data is accurately recorded and aggregated so an accurate assessment and prognosis may be made.

Wound Healing Evaluations

Therapeutic analyses for post operative wounds, traumatic wounds, ulcers, burns, scars, etc. collectively "wounds" can be made using this device. Measurements of the "wounds" at the outset of therapy and then at specific intervals of time allow for accurate evaluation of the progression of healing time and patient responsiveness to treatment. Topical and internal medicines can be studied for their effectiveness over time. These evaluations and resulting analyses can be viewed, collated, and cross referenced in an easy and efficient manner such that time is minimized, data accurately recorded and aggregated for efficient and accurate assessments and prognosis made.

Remote Diagnostic Evaluations

This device will allow for both local and remote medical and cosmetic consultations. These evaluations and applications can be shared effectively using store-and-forward telemedicine techniques. The TIP data set can be viewed, collated, and cross referenced in an easy and efficient manner such that patient and doctor time is minimized, data accurately recorded and aggregated and thus efficient and accurate diagnoses.

Accordingly the following are a list, not inclusive, of those ailments, maladies and concerns that can be addressed by the device as disclosed herein: Disorders relating to and/or resulting from: altered reactivity; bacterial and fungal diseases; cell kinetics; cell differentiation; drugs and chemical agents; epidermal cohesion; epidermal appendages and related disorders; epidermal and appendageal tumors; hematology; infestations, bites, and stings; lymphomas and pseudolymphomas; mechanical and physical factors; melanocytes; mucocutaneous integument; neoplasems; nutrition, metabolism, and genetics; organ systems: gastrointestinal, cardiovascular, pulmonary, endocrine, renal and other organ systems; persistent inflammation; rheumatology; including but not limited to sexually transmitted diseases.

Also identifiable are conditions of surgical dermatology, including but not limited to: cryosurgery; hair loss and transplant; liposuction; micrographic surgery; nail surgery; sclerotherapy; skin resurfacing; soft tissue augmentation and wounds.

Particularly the following, but not limited thereto, are capable of being identified through the use of the invention disclosed herein:

Abscess, Child Abuse, Drug Abuse, skin lesions, Physical Acantholytic Dermatosis, Transient Acanthosis Nigricans; Acarophobia; Acatalasia, Achromia Parasitica; Acne Artificialis; Acne Conglobata; Acne Cosmetica; Acne Excoriee; Acne Fulminans; Acne Keloidalis; Acne Mechanica; Acne Necrotica; Acne Neonatorum; Acne Rosacea; Acne Varioliformis; Acne Vulgaris; Chloracne; Cystic Acne, Halogen Acne, Pomade Acne, Steroid Acne, Tropical Acne, Acneiform Eruptions, Drug-Related Acne; Acrochordon; Acrocyanosis; Acrodermatitis Chronica Atrophicans; Acrodermatitis Continua; Acrodermatitis Enteropathica; Acrodermatitis of Hallopeau; Acrodermatitis Pustulosa Perstans; Papular Acrodermatitis of Childhood, Acrodynia; Acrokeratoelastoidosis; Acrokeratosis Verruciformis, Acromegaly, Acropachyderma, Acropustulosis, Acropustulosis Of Infancy, Acrosclerosis, Actinic Cheilitis, Actinic Dermatitis, Actinic Elastosis, Actinic Keratosis, Actinic Damage; Actinic Prurigo; Actinic Reticuloid; Actinomycosis, Actinophytosis, Acuminate Warts; Acute Febrile Neutrophilic Dermatoses, Drug Addiction, Addison's Disease; Sweat Gland Adenoma, Adenoma Sebaceum, Adenomatosis Oris, Adiposis Dolorosa, Agammaglobulinemia, AIDS, AIDS-Associated Syndromes, Ainhum, Albinism, Albright's Syndrome, Aldrich's Syndrome, Alkaptonuria, Allergic Contact Dermatitis, Allergic Vasculitis; Alopecia Areata, Alopecia Mucinosa, Alopecia Totalis, Alopecia Universalis, Androgenetic Alopecia, Scarring Alopecia, Amebiasis, Amputation Stump Dermatitis, Amyloidosis, Anagen Effluvium, Anaphylactoid Purpura, Anderson-Fabry Disease, Anemia, Anetoderma, Angiitis, Angioedema, Angiofibroma, Angioimmunoblastic Lymphadenopathy; Angiokeratoma & Other Benign Vascular Tumors; Angiokeratoma Corporis Diffusum, Angiolipoma, Angiolymphoid Hyperplasia, Angioma, Angioma Serpiginosum, Angioneurotic Edema, Anhidrotic Ectodermal Dysplasia, Animal Bites, Anthrax, Antiphospholipid Syndrome, Aphthous Ulcer, Aplasia Cutis Congenita, Apocrine Miliaria, Argyria, Arsenical Keratoses, Arteriolitis, Arteriovenous Malformations, Arthritis, Arthropod Bites And Stings, Ashy Dermatosis, Aspergillosis, Asteatosis, Ataxia-Telangiectasia, Atopic Dermatitis, Atrophic Nail Disorders, Malignant Atrophic Papulosis, Atrophie Blanche, Anetoderma, Atrophy Unclassified, Atypical Fibroxanthoma, Atypical Mycobacterial Infections, Auricular Fistula, Autoeczematous Dermatitis, Autoerythrocyte Sensitization, Autosensitization Dermatitis, Pustular Bacterid, Balanitis Xerotica Obliterans; Balding, Basal Cell Carcinoma, Basal Cell Nevus Syndrome, Battered Child, Bazin's Disease, B-Cell Disorders, Becker's Nevus, Behcet's Syndrome, Bejel, Benign Familial Chronic Pemphigus, Benign Mucous Membrane Pemphigoid, Benign Tumors, Berloque Dermatitis, Biliary Cirrhosis, Birthmarks, Insect Bites, Spider Bites, B-K Mole Syndrome, Black Hairy Tongue, Black Heel, Blaschko Dermatitis, North American Blastomycosis, South American Blastomycosis, Blepharitis, Blister Agents, Blister Beetle Dermatitis, Blood Dyscrasias, Bloom's Syndrome, Blue Nevus, Blue Rubber Bleb Nevus, Bockhart's Impetigo, Boil, Bornholm Disease, Botryomycosis, Bourneville's Disease, Bowenoid Papulosis, Bowen's Disease Or Intraepidermal Carcinoma, Branchial Cyst, Branchiogenic Cyst, Brazilian Pemphigus, Bromoderma, Brucellosis, Buerger's Disease, Bullous Dermatosis Of Childhood, Bullous Diabeticorum, Bullous Disorders, Bullous Pemphigoid, Burn, Buruli Ulcer, Buschke-Ollendorff Syndrome, Cafe-Au-Lait Spots, Caffey's Syndrome, Calcifying Epithelioma, Calcinosis Cutis And Osteoma Cutis, Callus, Campbell De'morgan Spot, Candidiasis, Canities, Canker Sore, Capillary Hemangioma, Carbuncle, Carcinoid Syndrome, Epidermoid Carcinoma, Metastatic Carcinoma, Merkel Cell Carcinoma, Squamous Cell Carcinoma, Carotenemia, Caterpillar Dermatitis, Cat-Scratch Disease, Cellulite, Lymphangitis, Dissecting Cellulitis of the Scalp, Cercarial Dermatitis, Chagas Disease, Chancre, Chancroid, Chédiak-Higashi Syndrome, Cheilitis, Cheilitis Glandularis, Cheilitis Granulomatosa, Chemical Blister Agents, Side-Effects of Cancer Chemotherapy, Cherry Angioma, Chickenpox, Chigger Bites, Chilblains, Child Abuse, Chloasma, Chloracne, Cholinergic Urticaria, Chondrodermatitis, Chromhidrosis, Chromoblastomycosis, Chromomycosis, Chronic Granulomatous Disease, Chrysiasis, Churg Strauss, Cicatricial Alopecia, Cicatricial Pemphigoid, Cicatrix, Clavus, Clear Cell Acanthoma, Clubbing Of Fingers, Cobb Syndrome, Coccidiodomycosis, Cockayne's Syndrome, Cold Injury, Ulcerative Colitis, Perforating Collagenosis, Collodion Baby; Colloid Milium, Comedos, Comedonal Nevus, Complement Deficiency Disorders, Compound Nevus, Condyloma Accuminatum; Condyloma Lata; Confluent And Reticulated Papillomatosis; Congenital Disorders, Unclassified; Congenital Fistulae; Congenital Hair Disorders, Unclassified; Congenital Hypoplasia; Congenital Poikiloderma; Congenital Self-Healing Reticulohistiocytosi; Congenital Syphilis; Congenital Vascular Neoplasm Syndromes; Connective Tissue Nevus; Conradi's Disease; Contact Dermatitis; Contracture; Unclassified; Copper Deficiency; Corns; Corticosteroid Effects; Cosmetic Procedures; Coumarin Reaction; Cowden's Disease; Coxsackie Infection; Craniofacial Angiomatosis; Creeping Eruption; Crest Syndrome; Crohn's Disease; Cronkhite-Canada Syndrome; Cryofibrinogenemia; Cryoglobulinemia; Cryosurgery; Cryptococcosis; Cushing's Syndrome; Cutaneomeningospinal Angiomatosis; Cutaneous B-Cell Lymphoma; Cutaneous Horn; Cutaneous Markers Of Malignancy; Cutaneous Papillomatosis; Cutaneous Tag; Cutaneous T-Cell Lymphoma; Cutis Elastica; Cutis Laxa; Cutis Marmorata; Cutis Marmorata Telangiectetica Congenita; Cutis Rhomboidalis Nuchae; Cutis Verticis Gyrata; Cyclic Neutropenia; Cylindroma; Cyst, Branchiogenic; Cyst, Epidermal Or Epithelial; Cyst, Keratinous, Pilar Or Sebaceous; Cyst, Mucous; Cyst, Pilar; Cyst, Sebaceous; Cyst, Synovial; Cytomegalovirus Infection; Dactylolysis; Dandruff; Darier-White Disease; Decubitus Ulcer; Deficiency, Mineral Or Vitamin; Degos Disease; Delusions Of Parasitosis; Demodex Folliculorum; Dental Abnormalities; Dental Sinus; Depigmentation; Depressive (Neurotic) Excoriations; Dercum's Disease; Dermal Hypoplasia; Dermatalgia; Dermatitis Herpetiformis; Dermatitis Medicamentosa; Dermatitis Nodularis Necrotica; Dermatitis Papillaris Capillitii; Dermatitis Repens; Dermatitis Vegetans; Dermatitis, Acute, Unclassified; Dermatitis, Atopic; Dermatitis, Autosensitization; Dermatitis, Beetle; Dermatitis, Berloque; Dermatitis, Contact; Dermatitis, Diaper; Dermatitis, Drug Allergy; Dermatitis, Drug Toxicity; Dermatitis, Dyshydrotic; Dermatitis, Eczematous; Dermatitis, Exfoliativa; Dermatitis, Facticial; Dermatitis, Infectious Eczematoid; Dermatitis, Irritant; Dermatitis, Nummular; ermatitis, Occupational; Dermatitis, Perioral; Dermatitis, Photo; Dermatitis, Pregnancy; Dermatitis, Radiation; Dermatitis, Seborrheic; Dermatitis, Stasis; Dermatitis, Nutritional; Dermatofibroma; Dermatofibrosarcoma Protuberans; Dermatofibrosis Lent Diss& Osteopoikilosis; Dermatolysis; Dermatomyositis; Dermatophyte Infections, Unclassified; Dermatophytid; Dermatophytosis; Dermatosis Papulosa Nigra; Dermographism; Dermoid Cyst; Desmoid Tumor; Desquamation, Unclassified; Diabetes Mellitus; Diabetic Dermodromes; Dialysis, Bullous Dermatoses Of Diaper Dermatitis; Disseminated Intravascular Coagulation; Diet & Dermatology; Digital Fibrokeratosis; Digitate Dermatoses; Diphtheria, Cutaneous; Discoid Lupus Erythematosus; Dissecting Cellulitis Of The Scalp; Disseminated Intravascular Coagulation; Disseminated Lupus Erythematosus; Disseminated Super. Actinic Porokeratosis; Discoid Lupus Erythematosus; Animal Bites; Down Syndrome; Dracunculosis; Drug Abuse; Drug Eruption; Drug Toxicity; Disseminated Superficial Actinic Porokeratosis; Duhring-Brocq Disease; Dupuytren's Contracture; Dyshydrotic Dermatitis; Warty Dyskeratoma; Dyskeratosis Congenita; Dyskeratosis Follicularis; Dysplastic Nevi Or Syndrome; Dysproteinemia; Dysraphism; Dystrophic Nails; Ecchymosis; Eccrine Gland Tumors; Eccrine Hydrocystoma; Eccrine Poroma; Eccrine Spiradenoma; Ecthyma; Ecthyma Contagiosum (Orf); Ecthyma Gangrenosum; Ectodermal Defect, Congenital; Eczema Craquele; Eczema Herpeticum And Vaccinatum; Eczema, Atopic; Eczema, Dyshydrotic; Eczema, Nummular; Edema, Angioneurotic; Edema, Legs, Hereditary; Edema, Unclassified; Ehlers-Danlos Syndrome; Ehrlichosis; Elastoidosis, Nodular With Cysts & Comedones; Elastolysis, Generalized; Elastoma, Juvenile; Elastosis Perforans Serpiginosa; Elastosis, Actinic; Elastosis, Perforating; Elephantiasis; Elephantiasis Nostras Verrucosa; Emboli;

Endocrinopathy, Miscellaneous; Endometriosis; Eosinophilic Fasciitis; Eosinophilic Granuloma; Eosinophilic Papulovesicular Derm Of Newborn; Ephelides And Lentigines; Epidermal Inclusion Cyst; Epidermal Necrolysis, Toxic; Epidermal Nevus; Epidermodysplasia Verruciformis; Epidermoid Carcinoma; Epidermolysis Bullosa; Epidermolytic Hyperkeratosis; Epiloia; Epithelial Cyst; Epithelial Nevus; Epithelioma Adenoides Cysticum; Epithelioma, Arsenical; Epithelioma, Basal Cell; Epithelioma, Calcifying Of Malherbe; Epithelioma, Squamous; Erosio Interdigitalis Blastomycetica; Eruption Of Lymphocyte Recovery; Eruption, Creeping; Erysipelas; Erysipeloid; Erythema Ab Igne; Erythema Annulare Centrifugum; Erythema Chronicum Migrans; Erythema Circinatum; Erythema Dyschromicum Perstans; Erythema Elevatum Diutinum; Erythema Figuratum Perstans; Erythema Gyratum Perstans; Erythema Gyratum Repens; Erythema Induratum; Erythema Infectiosum; Erythema Marginatum; Erythema Multiforme; Erythema Nodosum; Erythema Of Jacquet; Erythema Perstans; Erythema Toxicum Neonatorum; Erythema, Anatomic; Erythema, Noninfectious, Unclassified; Erythema, Toxic; Erythema, Unclassified; Erythermalgia; Erythrasma; Erythrocyte Autosensitization; Erythroderma, Exfoliative; Erythrokeratodermia Variabilis; Erythromelalgia; Erythroplasia Of Queyrat; Esthiomene; Exanthem Subitum; Exanthem, Bacterial; Exanthem, Viral; Excoriation, Depressive Or Neurotic; Exfoliation Of Palms And Soles; Exfoliative Dermatitis (Or See Cause); Extramammary Paget's Disease; Extramedullary Hematopoeisis, Cutaneous; Exudative Discoid And Lichenoid Derrnatitis; Fabry's Disease; Facial Granuloma; Facticial Dermatitis; Familial Benign Chronic Pemphigus; Familial Hemorrhagic Telangiectasia; Farber's Disease; Fasciitis, Necrotizing; Fat Dystrophy; Fat Necrosis; Favre-Racouchot Elastoidosis Syndrome; Favus; Febrile Neutrophilic Dermatosis, Acute; Female Pattern Baldness; Fever Blisters, Aphthae; Fever Blisters, Herpes Simplex; Fibroepithelial Polyp; Fibroma; Fibromatosis Of Penis; Fibrous Papule Of Nose; Fibroxanthoma, Atypical; Fifth Disease; Figurate Erythema; Filariasis; Fissured Tongue; Fistulae, Congenital; Fixed Drug Eruption; Flat Warts; Flea Bites; Florid Oral Papillomatoses; Flushing, Non-Carcinoid; Focal Dermal Ilypoplasia; Fogo Selvagem; Follicular Mucinosis; Folliculitis; Folliculitis Abscedens Et Suffodiens; Folliculitis Decalvans; Folliculitis Keloidalis; Fordyce Lesions Of Scrotum; Fordyce Spots; Foreign Body; Foreign Body Granuloma; Fox-Fordyce Disease; Freckles; Friction Blister; Frostbite; Fungal Cultures (Alphabetical By Genus); Fungal Infection, Deep, Unclassified; Fungal Infection, Superficial, Unclassified; Furuncle; Ganglion; Gangosa; Gangrene; Gardner's Syndrome; Gargoylism; Gastrointestinal Syndromes; Gaucher's Disease; Geographic Tongue; German Measles' Gi Disease, Skin; Manifestations; Gianotti-Crosti Syndrome; Giant Cell Arteritis; Gingiva, Unclassified; Gingival Hypertrophy; Gingivitis, Unclassified; Glanders; Glandular Cheilitis; Glomus Tumor; Glossitis, Median Rhomboid; Glossitis, Unclassified; Glucagonoma Syndrome; Glycogen Storage Disease; Gold Pigmentation; Goltz Syndrome; Gonococcemia; Gonorrhea; Gougerot-Blum Disease; Gougerot-Carteaud's Papillomatosis; Gout; Gower's Panatrophy; Graft Vs. Host Reaction; Granular Cell Myoblastoma; Granuloma; Annulare; Granuloma Faciale; Granuloma Fissuratum, Cutaneous; Granuloma Fissuratum, Mouth; Granuloma Inguinale; Granuloma Pyogenicum; Granuloma, Mosinophilic; Granuloma, Foreign Body; Granuloma, Meischer's; Granuloma, Swimming Pool; Granuloma, Unclassified; Granulomatosis Disciformis, Meischer; Granulomatosis, Chronic Familial; Granulomatosis, Wegener's; Granulomatous Disease, Chronic; Granulosis Rubra Nasi; Graves Disease; Grooved Tongue; Grovers Disease; Gumma; Guttate Hypomelanosis, Idiopathic; Guttate Morphea; Gynecomastia; Gypsy Moth Dermatitis; Hailey-Hailey Disease; Hair Collar Sign; Hair Excess; Hair Pigment Disorder; Hair Shaft Abnormalities; Hairy Leukoplakia (Aids Associated); Hairy Leukoplakia (Non-Aids Associated); Hairy Tongue; Halo Nevus; Halogen Acne; Hamartoma; Hand And Foot Eruption, Unclassified; Hand-Foot-And-Mouth Disease; Hand-Schuller-Christian Disease; Hansen's Disease; Hartnup Disease; Heat Injury; Heat Rash; Hemangiectatic Hypertrophy; Hemangioendothelioma; Hemangioma; Hematologic Disorders, Unclassified; Hematoma; Hemochromatosis; Hemosiderosis; Henoch-Schonlein Purpura; Hepatic Disease; Hepatitis; Hereditary Disorders, Unclassified; Hereditary Hemorrhagic Telangiectasia; Herpangina; Herpes Gestationis; Herpes Progenitalis; Herpes Simplex; Herpes Zoster; Hibemoma; Hidradenitis Suppurativa; Hidradenitis, Palmar-Plantar; Hidradenoma Papilliferum; Hidrocystoma; Hidrotic Ectodermal Defect; Hippocratic Nails; Hirsuitism; Histicytoma; Histiocytoid Hemangioma; Histiocytosis X; Histoplamosis; Hives; Hodgkin's Disease; Homocystinuria; Hookworm Infestations; Horn, Cutaneous; Housewife's Eczema; Howell Evans Synd; Hunter's Syndrome; Hurler's Syndrome; Hyalinosis Cutis Et Mucosae; Hydroa Aestivale; Hydroa Vacciniforme; Hygroma, Cystic; Hyper Ige Syndrome; Hypercholesterolemia; Hyperhydrosis; Hyperkeratosis Climactericum; Hyperkeratosis Follicularis (Kyrle's); Hyperkeratosis Lenticularis Perstans (Flegel); Hyperkeratosis Palmaris Et Plantaris; Hyperkeratosis, Epidermolytic; Hyperkeratosis, Unclassified; Hyperlipemia; Hyperpigmentation, Unclassified; Hypersensitivity Vasculitis; Hypertrichosis; Hypertrophic Nails; Hypertrophic Scar; Hypertrophy From Chronic Irritation; Hypohidrosis; Hypomelanosis, Unclassified; Hypoplasia, Congenital; Ichthyosis; Ichthyosis Hystrix; Ichthyosis Linearis Circumflex; Ichthyosis Vulgaris; Id Eruption; Idiopathic Guttate Hypomelanosis; Ige Syndrome; Immersion Foot; Immune Complex Disease; Immune Deficiency, Acquired (AIDS); Immune Deficiency, Unclassified (Not AIDS); Immunoblastic Lymphadenopathy; Immunoglobulin Deficiency Disorders; Impetigo, Impetigo Follicularis; Impetigo Herpetiformis; Impetigo Of Bockhart; Inclusion Cyst; Incontinentia Pigmenti; Infantile Lichenoid Dermatitis; Infections, Bacterial, Unclassified; Infections, Rickettsial, Unclassified; Infections, Viral, Unclassified; Infectious Eczematoid Dermatitis; Infectious Mononucleosis; Infundibulofolliculitis; Injury, Traumatic; Inoculation Tuberculosis; Insect Bites And Stings; Intaepidermal Carcinoma; Intertrigo; Iododerma; Irritant Dermatitis; Ischemia; Ischemic Ulcer; Itch, Unclassified; Jadassohn-Lewandowsky Syndrome; Jaundice; Jaw, Lumpy; Jellyfish Sting; Jessner's Lymphocytic Infiltration; Job's Syndrome; Junctional Nevus; Juvenile Elastoma; Juvenile Melanoma, Benign; Juvenile Xanthogranuloma; Kala Azar; Kaposi's Sarcoma (Aids Associated); Kaposi's Sarcoma (Not Aids Associated); Kaposi's Varicelliform Eruption; Kasaback-Merritt Syndrome; Kawasaki Disease; Keloid; Keloid Acne; Keloidal Blastomycosis; Keratinous Cyst; Keratoacanthoma; Keratoderma Blenorrhagica; Keratoderma Climactericum; Keratoderma Of Palms And Soles; Keratoderma Palmaris Et Plantaris; Keratolysis Exfoliativa; Keratolysis, Pitted; Keratosis Blenorrhagica And Reiter's Synd; Keratosis Follicularis; Keratosis Palmaris Et Plantaris; Keratosis Pilaris; Keratosis Punctata Palmaris Et Plantaris; Keratosis, Actinic; Keratosis, Follicle, Unclassified; Keratosis, Mouth; Keratosis, Seborrheic; Keratosis. Arsenical; Kerion; Kinky Hair Disease, Menke's; Klippel-Trenaunay-Parkes-Weber; Knuckle Pads; Koh Preparation; Koilonychia; Kraurosis Vulvae; Kwashiorkor; Kyrle's Disease; Lamellar Dyshydrosis; Lamellar Ichthyosis; Larva Migrans; Laser Therapy; Leg Ulcer, Unclassified; Leiner's Disease; Leiomyoma; Leishmaniasis; Lentigo; Lentigo Maligna; Lentigo Maligna Melanoma; Leopard Syndrome; Leprosy; Lesch-Nyhan Syndrome; Leser-Trélat Sign; Lethal Midline Granuloma; Letterer-Siwe Disease; Leukemia Cutis; Leukocyte Disorders, Unclassified; Leukoderma, Unclassified; Leukonychia; Leukoplakia And Keratosis, Mouth; Leukoplakia, Except Mouth; Lichen Amyloidosis; Lichen Aureus; Lichen Myxedematosis; Lichen Nitidus; Lichen Pilaris; Lichen Planopilaris; Lichen Planus; Lichen Sclerosus Et Atrophicus; Lichen Scrofulosorum; Lichen Simplex Chronicus; Lichen Spinulosus; Lichen Striatus; Light Eruption Or Reaction; Light Therapy; Lindau-Von Hippel Disease; Linear & Whorled Nevoid Hyperpigmentation; Linear Iga Disease; Linear Nevus; Lip, Unclassified; Lipoatrophy; Lipodystrophy; Lipogranulomatosis; Lipoid Proteinosis; Lipoma; Livedo Reticularis; Loaisis; Lobo's Disease; Loxoscelism; Lumpy Jaw; Lupus Erythematosus, Discoid; Lupus Erythematosus, Neonatal; Lupus Erythematosus, Subacute Cutaneous; Lupus Erythematosus, Systemic; Lupus Miliaris Disseminata; Lupus Miliaris Disseminata Faciei; Lupus Pernio; Lupus Profundus; Lupus Vulgaris; Lyell's Syndrome; Lyme Disease; Lymphadenosis Cutis; Lymphangioma; Lymphangitis; Lymphedema; Lymphoblastoma; Lymphocyte Recovery Eruption; Lymphocytic Infiltrate Of Jessner; Lymphocytoma Cutis And Lymphocytic Infilt.; Lymphogranuloma Venereum; Lymphoma, Hodgkin's; Lymphoma, Non-Hodgkin's, Other; Lymphomatoid Granulomatosis; Lymphomatoid Papulosis; Macrochelia; Macroglobulinemia; Macroglossia; Maculae Ceruleae; Macular Atrophy; Madelung's Disease; Madura Foot; Maduromycosis; Mafucci's Syndrome; Majocchi's Disease; Majocchi's Granuloma; Mal De Meleda; Mal Perforans Ulcer; Male Pattern Baldness; Malherbe, Calcifying Epithelioma Of; Malignancy Markers, Cutaneous; Malignant Atrophic Papulosis; Malignant Freckle; Malignant Lentigo; Malignant Melanoma; Malignant Tumors, Unclassified; Marfan's Syndrome; Marjolin's Ulcer; Markers Of Malignancy, Unclassified; Mast Cell Tumor; Mastocytosis; Measles; Measles, German; Median Rhomboid Glossitis; Meischer's Granuloma; Melanoma, Lentigo Maligna; Melanoma, Malignant; Melanosis Circumscripta Precancerosa; Melasma; Melkersson-Rosenthal Syndrome; Meloidosis; Meningococcemia; Menkes Kinky Hair Syndrome; Mercury Pigmentation; Merkel Cell Carcinoma; Metal Allergy; Metal Pigmentation; Metastatic Carcinoma; Mibelli, Angiokeratoma Of; Microscopic Examination; Midline Granuloma, Lethal; Miliaria; Milium; Milker's Nodules; Milroy's Disease; Mite Dermatitis; Mixed Connective Tissue Disease; Mohs Micrographic Surgery; Mole; Molluscum Contagiosum; Mondor's Syndrome; Mongolian Spot; Mongolism; Monilethrix; Moniliasis; Morbus Moniliformis; Morphea; Morquio's Disease; Mucha-Habermann's Disease; Mucinosis, Focal; Mucinosis, Reticular Erythematous; Mucinous Cyst; Mucocutaneous Lymph Node Syndrome; Mucopolysaccharidoses; Mucormycosis; Mucosa, Oral, Unclassified; Mucous Cyst; Multicentric Reticulohistiocytosis; Multiple Benign Cystic Epithelioma; Multiple Endocrine Neoplasia Synd; Multiple Hamartoma Syndrome; Multiple Idiopathic Hemorrhagic Sarcoma; Multiple Mucosal Neuroma; Multiple Myeloma; Mumps; Munchausen Syndrome; Mycetoma; Mycobacterial Infections, Atypical; Mycosis Fungoides; Myiasis; Myoblastoma; Myoepithelioma; Myoma And Leiomyoma; Myxedema And Localized Myxedema; Myxoid Cyst; Nail Disorders Assoc. With Internal Disease; Nail Dystrophy, Unclassified; Nail Pits; Nails, Normal Variants; Narcotic Dermopathy; Nasal Glioma; Necrobiosis Lipoidica; Necrobiotic Xanthogranuloma; Necrolysis, Toxic Epidermal; Necrolytic Migratory Erythema; Necrosis, Unclassified; Necrotizing Fasciitis; Necrotizing Vasculitis; Needle Marks; Neonatal Acne; Neonatal Lupus Erythematosus; Netherton's Syndrome; Neurilemmoma; Neurodermatitis; Neurofibroma, Neurofibromatosis; Neurotic Excoriations; Neutrophilic Dermatosis, Acute Febrile; Nevoxanthoendothelioma; Nevoxanthogranuloma; Nevus Anemicus; Nevus Angiolipomatosus; Nevus Araneus; Nevus Caeruleus; Nevus Cell Nevus; Nevus Comedonicus; Nevus Depigmentosus; Nevus Elasticus; Nevus Flammeus; Nevus Of Ito; Nevus Of Ota; Nevus Sebaceous; Nevus Syringocystadenoma Papilliferum; Nevus Unius Lateris; Nevus, Blue; Nevus, Blue Rubber Bleb; Nevus, Compound; Nevus, Dermal; Nevus, Epidermal; Nevus, Epithelial; Nevus, Halo; Nevus, Junctional; Nevus, Linear; Nevus, Organoid; Nevus, Pigmented; Nevus, Spider; Nevus, Spindle Cell; Nevus, Verrucous; Nevus, White Spongy Of Mucosa; Nickle Allergy; Niemann-Pick Disease; Nocardiosis; Nodular Dermal Allergide; Nodular Elastoidosis; Nodular Fasciitis; Nodular Fat Necrosis; Nodular Subepidermal Fibrosis; Nodular Vasculitis; Nodules, Milker's; Nodules, Rheumatoid; Noma; Non-Venereal Treponematoses; Normal Variants; North American Blastomycosis; Norwegian Scabies; Nummular Dermatitis; Nutritional Or Vitamin Deficiency; Occupational Acne; Occupational Dermatoses, Unclassified; Occupational Leukoderma; Ochronosis; Ocular Pemphigus; Oid-Oid Disease; Omphalitis; Onchocerciasis; Onychauxis; Onychia; Onychodystrophy, Unclassified; Onychogryphosis; Onycholysis; Onychomycosis; Ophiasis; Oral Florid Papillomatoses; Oral Mucosa, Unclassified; Oral Tumors; Oral, Unclssified; Oral-Facial-Digital Syndrome; Orf; Organoid Nevus; Oroya Fever; Osler-Rendu-Weber Disease; Osteoarthritis; Osteodermatopoikilosis; Osteogenesis Imperfecta; Osteoma Cutis; Other Syndromes, Unclassified; Oxyuriasis; Pachydermoperiostosis; Pachyonychia Congenita; Pagetoid Reticulosis; Paget's Disease; Painful Bruising Syndrome; Palate, Unclassified; Palmar Erythema; Palmar Fibromatosis; Palmar-Plantar Hidradenitis; Palmoplantar Keratosis; Palmoplantar Pustulosis, Unclassified; Panatrophy Of Gower; Paimiculitis; Papilloma, Mucous Membrane; Papilloma, Skin; Papillomatoses, Cutaneous; Papillomatoses, Florid Oral; Papillon-Lefévre Syndrome; Papular Dermatitis Of Pregnancy; Papular Mucinosis; Papular Urticaria; Papulonecrotic Tuberculid; Papulosis, Malignant Atrophic Of Degos; Paracoccidioidomycosis; Paraffinoma; Paraneoplastic Syndromes; Parapsoriasis, Acute; Parapsoriasis, Chronic; Parasitic Infestations, Unclassified; Parasitosis, Delusions Of, Paronychia; Pasini Et Pierini Syndrome; Patch Testing, Pathergic Granulomatosis; Pearly Penile Papules; Pediatric Dermatoses; Pediculosis; Pelade; Pellagra; Pemphigoid, Benign Mucous Membrane; Pemphigoid, Bullous; Pemphigoid, Cicatricial, Mucosal; Pemphigoid, Unclassified; Pemphigus Erythematodes; Pemphigus Foliaceusp; Pemphigus Vegetans; Pemphigus Vulgaris; Pemphigus, Brazilian; Pemphigus, Drug; Pemphigus, Familial Benign Chronic; Pemphigus, Hailey-Hailey; Pemphigus, Unclassified; Penile Pearly Papules; Perforating Collagenosis; Perforating Dermatosis; Perforating Folliculitis; Periadenitis Mucosa Necrotica Recurrans; Perianal Protrusions, Pyramidal; Perianal Strep; Periarteritis Nodosa; Perifolliculitis Capitis Abscedens Et Suff.; Perioral Dermatitis; Perléche; Pernicious Anemia; Pernio; Petechiae;

Peutz-Jeghers Syndrome; Peyronie's Disease; Phagedena; Phenylketonuria; Phlebectasia; Phlebitis; Phototherapy; Phrynoderma; Phthiriasis; Phycomycosis; Pian; Piebaldism; Piedra; Piezogenic Pedal Papules, Painful; Pigmentary Hairy Nevus; Pigmentation, Anatomic; Pigmentation, Hair; Pigmentation, Nail; Pigmentation, Unclassified; Pigmented Purpuric Eruptions; Pilar Cyst; Pilar Tumor; Pilomatricoma; Pilonidal Cyst; Pinta; Pinworm Dermatitis; Pitted Keratolysis; Pitted Nails; Pityriasis Alba; Pityriasis Capitis; Pityriasis Lichenoides Chronica; Pityriasis Lichenoides Et Varioliformis Acuta; Pityriasis Rosea; Pityriasis Rubra Pilaris; Pityriasis Streptogenes; Pityriasis Versicolor; Plant Dermatitis, Plantar Wart; Plasmacytoma; Pleva; Podagra; Poikiloderma; Poikiloderma Congenitale; Ploikiloderma Of Civatte; Poikiloderma Vasculare Atrophicans; Poison Ivy Dermatitis; Poliosis; Polyarteritis Nodosa; Polychondritis; Polycythemia Vera; Polydactyly; Polymorphic Light Eruption; Polyostotic Fibrous Dysplasia (Albright's); Polyp, Fibroepithelial; Pompholyx; Porokeratosis; Poroma; Porphyria; Port Wine Stain; Portugese Man-Of-War Sting; Post-Inflammatory Hyperpigmentation; Post-Inflammatory Hypopigmentation; Postmastectomy Lymphangiosarcoma; Pregnancy, Dermatitis In; Pressure Sore; Pretibial Myxedema; Prickle Cell Carcinoma; Prickly Heat; Primary Syphilis; Progeria; Progressive Bacterial Synergistic Gangrene; Progressive Pigmentary Dermatoses; Proteinosis, Lipoid; Prurigo Gestationis; Prurigo Gravidarum; Prurigo Nodularis; Pruritic Urticarial Papules Plaques Of Preg.; Pruritis, Signs, Unclassified; Pruritus Gravidarum; Pseudoacanthosis Nigricans; Pseudoatrophoderma Colli; Pseudocyst Of The Auricle; Pseudofolliculitis Barbae; Pseudolymphoma Of Speigler-Fendt; Pseudomonas Infection; Pseudopelade; Pseudosarcoma; Pseudotuberculosis; Pseudoverrucous Papules; Pseudoxanthoma Elasticum; Psoriasis; Pterygium; Punctate Keratosis Of Palms And Soles; Puppp Syndrome; Purpura And Ecchymosis; Purpura Annularis Telangiectoides; Purpura Fulminans; Purpura Pigmentosa Chronica; Purpura Rheumatica; Purpuric Pigmented Lichenoid Dermatitis; Pustular Bacterid; Pustular Dermatosis, Subcorneal; Pustular Eruption Of Palms And Soles; Pustular Perifolliculitis; Pustulosis Palmaris Et Plantaris; Pyoderma And Folliculitis; Pyoderma Faciale; Pyoderma Gangrenosum; Pyogenic Granuloma; Pyramidal Perianal Protrusion; Radiation Dermatoses; Radiation Therapy; Ragweed Dermatitis; Ranula; Raynaud's Disease Or Phenomenon; Reactive Perforating Collagenosis; Reflex Sympathetic Dystrophy; Reiter's Syndrome; Relapsing Polychondritis; Relapsing Self-Healing Blaschko Dermatitis; Rem Syndrome; Rendu-Osler-Weber Syndrome; Retention Cysts Of Lips; Reticular Erythematous Mucinosis; Reticulohistiocytosis, Multicentric; Reticulohistiocytosis, Cong Self-Healing; Reticuloid, Actinic; Reticulum Cell Sarcoma; Rheumatoid Arthritis; Rheumatoid Nodule; Rhinophyma; Rhinoscleroma; Rhinosporidiosis; Rhus Dermatitis; Rickettsial Infections; Riehl's Melanosis; Ringed Hair; Ritter's Disease; Rocky Mountain Spotted Fever; Rodent Ulcer; Romberg's Disease; Rosacea; Rosacea-Like Tuberculid Of Lewandowsky; Roseola Infantum; Rothman-Makai Syndrome; Rothmund-Thomson Syndrome; Rubella; Rubeola; Sarcoid; Sarcoma; Sarcoma, Kaposi's (Aids-Associated); Sarcoma, Kaposi's (Not Aids); Sauriasis; Scabies; Scalded Skin Syndrome; Scar; Scarlet Fever; Schamberg's Disease; Schistosomiasis; Scleredema; Sclerema; Sclerodactyly; Scleroderma; Sclerodermatomyositis; Scleromyxedema; Sclerosing Hemangioma; Sclerosing Lymphangitis, Penis; Sclerosis, Diffuse Systemic; Sclerotherapy; Scratch Marks; Scrofuloderma; Scrotal Tongue; Scurvy; Seabather's Eruption; Sebaceous Adenoma; Sebaceous Cyst; Sebaceous Epithelioma; Sebaceous Gland Carcinoma; Sebaceous Gland Tumors, Benign; Sebaceous Hyperplasia; Sebaceous Nevus; Seborrheic Dermatitis; Seborrheic Keratosis; Secondary Syphilis; Senear-Usher Syndrome; Senile Elastosis; Senile Keratosis; Senile Purpura; Septicemia; Serum Sickness; Sezary Syndrome; Shingles; Sickle Cell Ulcer; Sjögren's Syndrome; Skin Tag; Skin Tests For Allergy; Smallpox; Snake Bites; Sneddon-Wilkinson Subcorneal Pustulosis; Solar Atrophy; Solar Keratosis; Solar Urticaria; South American Blastomycosis; Speigler-Fendt Sarcoid; Spider Bites; Spider Nevi; Spinal Dysraphism; Spindle Cell Nevus; Spiradenoma; Spitz's Juvenile Melanoma; Sporotrichosis; Squamous Cell Carcinoma; Staphylococcal Scalded-Skin Syndrome; Stasis Dermatitis; Steatocytstoma Multiplex, Steroid Acne, Steroid Effects, Unclassified; Stevens-Johnson Syndrome; Stings, Insect; Stings, Other Than Insects And Spiders; Stings, Spider; Stomatitis; Stomatitis, Aphthous; Storage Disease, Glycogen; Striae; Stucco Keratosis; Stump Dermatitis; Sturge-Weber Syndrome; Subacute Bacterial Endocarditis; Subcorneal Pustular Dermatosis; Subcutaneous Fat Necrosis; Subepidermal Nodular Fibrosis; Sulzberger-Garbe Disease; Sunburn; Supernumerary Digit; Supernumerary Nipple; Surfer's Nodule; Surgery; Sweat Gland Carcinoma; Sweat Gland Disorders, Unclassified; Sweat Gland Necrosis; Sweat Gland Tumors, Benign; Sweet's Syndrome; Swimmer's Itch; Swimming Pool Granuloma; Sycosis; Symmetric Lividity Of The Soles; Symmetrical Peripheral Gangrene; Syndactyly; Synovial Cyst; Syphilis, Congenital; Syphilis, Primary; Syphilis, Secondary; Syphilis, Tertiary; Syringocystadenoma Papilliferum; Syringoma; Systemic Lupus Erythematosus; Systemic Therapy; Tags, Skin; Tar Melanosis; Tattoo; T-Cell Disorders; Teaching Slides; Teeth Abnormalities, Unclassified; Telangiectasia; Telangiectasia Macularis Eruptiva Perstans; Telangiectasia, Hereditary Hemorrhagic; Telogen Effluvium; Temporal Arteritis and other such like diseases and maladies now known and unknown.

Without doubt the invention disclosed herein served many well and long felt needs and concerns among the public and health care professionals.

OBJECTS OF THE INVENTION

In view of the foregoing, it is therefore an object of the invention to provide a detection device for skin cancer and other diseases of the skin.

It is a further objective of the invention to provide a detection device for skin cancer and other maladies of the skin that is neither invasive nor destructive to the tissue being examined.

A further object of a preferred embodiment of the invention is to provide a device that may be used as a mirror for anyone wishing to view his/her body but have been unable to do so, such as in gym facilities, homes, physician's offices, and other health care facilities.

A further object of a preferred embodiment of the invention is to provide detection means that does not involve biopsy or contact with the skin.

Another object of a preferred embodiment of the invention is to provide detection means that does not have side effects on the skin.

A further object of a preferred embodiment of the invention is to provide a means for remote viewing of patients for telemedical diagnostic means, such as in prison facilities, remote locations or other areas that are similarly deficient in highly qualified or experts in a medical field.

A further object of a preferred embodiment of the invention is to provide a cost-effective device.

Another object of a preferred embodiment of the invention is to provide a device that may be easy to employ.

A further object of a preferred embodiment of the invention is to provide a device that may be assembled with minimal professional carpenter assistance.

A further object of a preferred embodiment of the invention is to provide a device that may be easily transportable.

Another object of a preferred embodiment of the invention is to provide a device that is capable of being used in a system for reducing maladies of the skin A further object of a preferred embodiment of the invention is to provide a device that allows for automated acquisition of human physiological characteristics.

A further object of a preferred embodiment of the invention is to provide a device that allows for melanoma and skin cancer screening.

A further object of a preferred embodiment of the invention is to provide a device that allows for POSI score calculation.

A further object of a preferred embodiment of the invention is to provide a device that allows for hair loss and/or growth evaluation (s).

A further object of a preferred embodiment of the invention is to provide a device that allows for wound healing evaluations.

A further object of a preferred embodiment of the invention is to provide a device that allows for remote diagnostic evaluations.

A further object of a preferred embodiment of the invention is to provide a device that allows for viewing and analysis of cosmetic surgery applications.

A further object of a preferred embodiment of the invention is to provide a device that allows for beauty evaluations.

A further object of a preferred embodiment of the invention is to provide a device that allows for body morphology analysis.

A further object of a preferred embodiment of the invention is to provide a device that allows for viewing and analysis of soft tissue augmentation.

A further object of a preferred embodiment of the invention is to provide heath care professionals with a device that will make doctor-patient interface time more efficient.

Another object of a preferred embodiment of the invention is to provide a device capable of allowing health care professional(s), doctor(s), nutritionist(s), physical trainer(s) and individual person(s) the ability to view, monitor, evaluate and render decisions based upon that which is captured, viewed and or compared to prior analysis utilizing the device as disclosed herein.

A further object of a preferred embodiment of the invention is to provide a device that may reduce patient time spent in a health care professional's, doctor's, nutritionist's, physical trainer's facility where said individual may review an his/her health, etc.

A further object of a preferred embodiment of the invention is to provide a device that may reduce the related costs associated with an analysis as described herein.

Another object of a preferred embodiment of the invention is to provide a device that may reduce the cost to insurance programs reimbursing applicable healthcare and related professions for their time and effort associated with the rendering of care to such an insured individual.

Another object of a preferred embodiment of the invention is to improve the quality of life.

Another object of the present device disclosed herein is to allow for a better and more efficient rendering of any of a variety of forms of health care where visualization of the human body, including parts thereof, is required.

The preferred embodiments of the invention thus provides a device for the identification, diagnosis and subsequent treatment of maladies of the skin that is time and cost efficient and effective with no side effects.

Having thus described the invention, it will be apparent to those of skill in the art that modifications can be made within the scope of the invention without departing from the scope or breath of that which is intended and disclosed herein.

DETAILED DESCRIPTION OF THE PREFERRED EMBODIMENT

This invention teaches a TIP device that provides non-occluded images by employing an array of imaging devices and thereafter combining individual images to form a continuous image. It has been heretofore contemplated that the device could find use as an aid in screening and diagnosis of conditions of soft tissue, hair and nails. Furthermore, it could also find use as a beauty aid to consult those considering cosmetic surgery or changes in personal appearance.

Thus, the following detailed description, read with the above-described drawings will serve to explain various preferred embodiments and components of the present invention.

Figure 1:
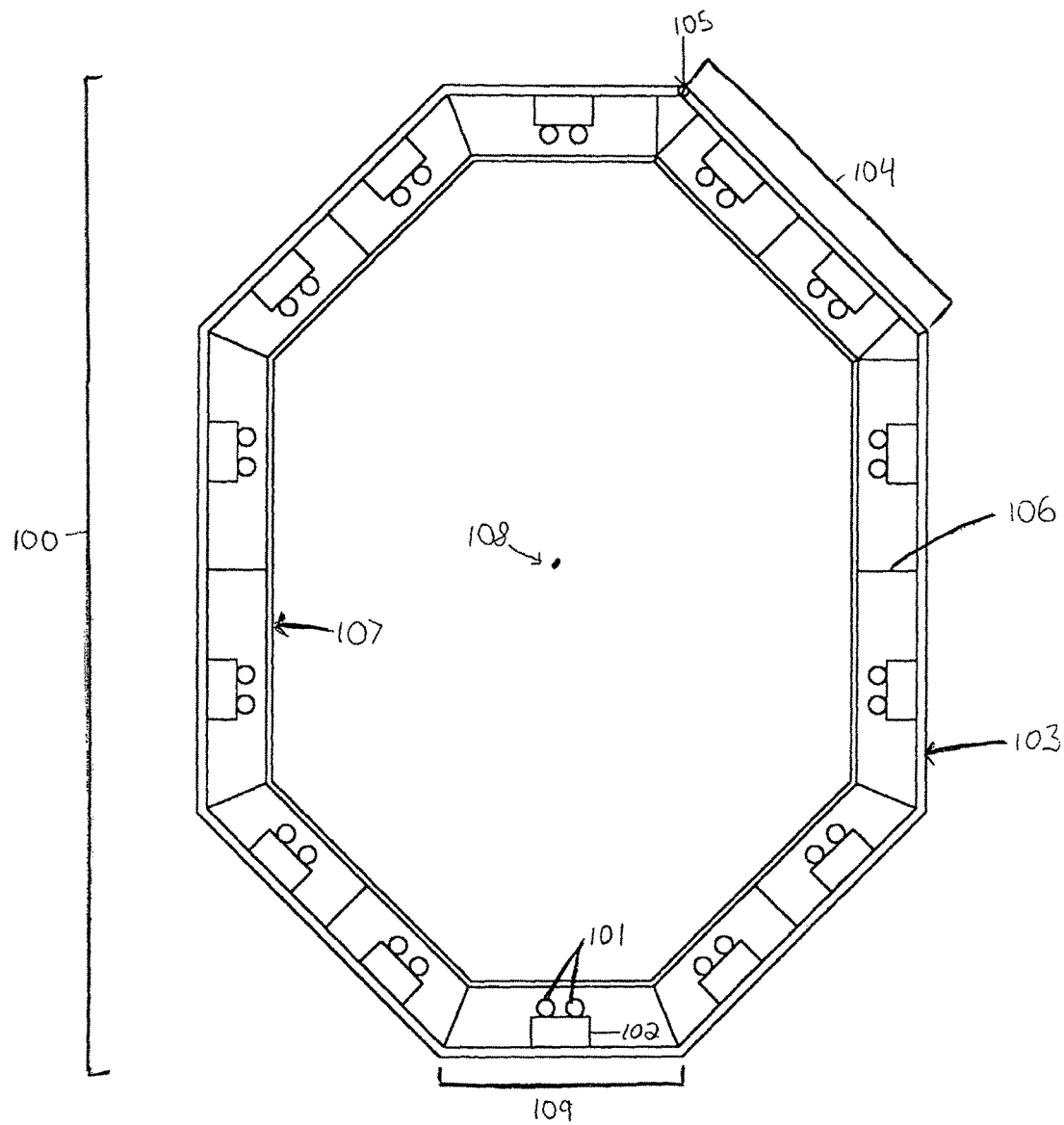
FIG. 1 depicts a horizontal cross-section of an imaging system in accordance with the present invention.

FIG. 1 depicts a horizontal cross section of an embodiment of the TIP system 100 in accordance with the present invention. The system may be sized in any fashion to accord with the application. For example, should the system be used to image an entire person, the system will be sized such that the person could easily stand at the center 108 of the device 100 with sufficient comfort. However, if the particular application is for the examination of something smaller, the scalp, for example, the device could be made smaller such that just a person's cranium would fit comfortably at center 108. The system 100 is comprised of several panels 109. In this particular embodiment, fourteen (14) panels are used. The panels are interconnected to form an enclosed structure. In this particular embodiment, an 8-sided polygon was chosen. The shape is arbitrary, however, the only requirement is that the panels are set up in mirrored pairs. Each panel 109 is comprised of an imager array 102, comprising a vertical array of imaging devices. The imaging devices could comprise standard or digital cameras, or other devices capable of capturing light, temperature, chemical information or other information of interest. In this embodiment, we assume the use of digital cameras operating in the conventional fashion. Thus, in order to optimize the performance of the cameras, light sources 101 are utilized. While fluorescent tubes are the preferred means, any type of illumination can be used, for example, a Wood's lamp may be used. These light sources 101 can be always on, or, alternatively, only activated when the cameras are operating. Supporting the imager array 102 is the perimeter wall 103. The perimeter wall can be made of plywood, particle board or any other structural material capable of supporting the structure. In front of the light sources 101 and imager array 102 is shield 107. Shield 107 protects the imager array 102 and light sources 101 from contact with the subject. Standard ⅛" obscured plexiglass can be used as shield 107, and furthermore, a shield with variable transmittance is contemplated. In between the plurality of panels 109, there are dividers 106. Dividers 106 function to provide stability for shield 107, and also, when made opaque, reduce light interference between adjacent imager arrays 102. To effect access and egress, panels 104 function as a doorway. By rotating on hinge 105, panels 104 swing outward, thus allowing access to the interior of system 100. A system 100 is also contemplated without doorway 104 that can be used for examining small objects, such as the scalp or hands, for example.

Figure 2:
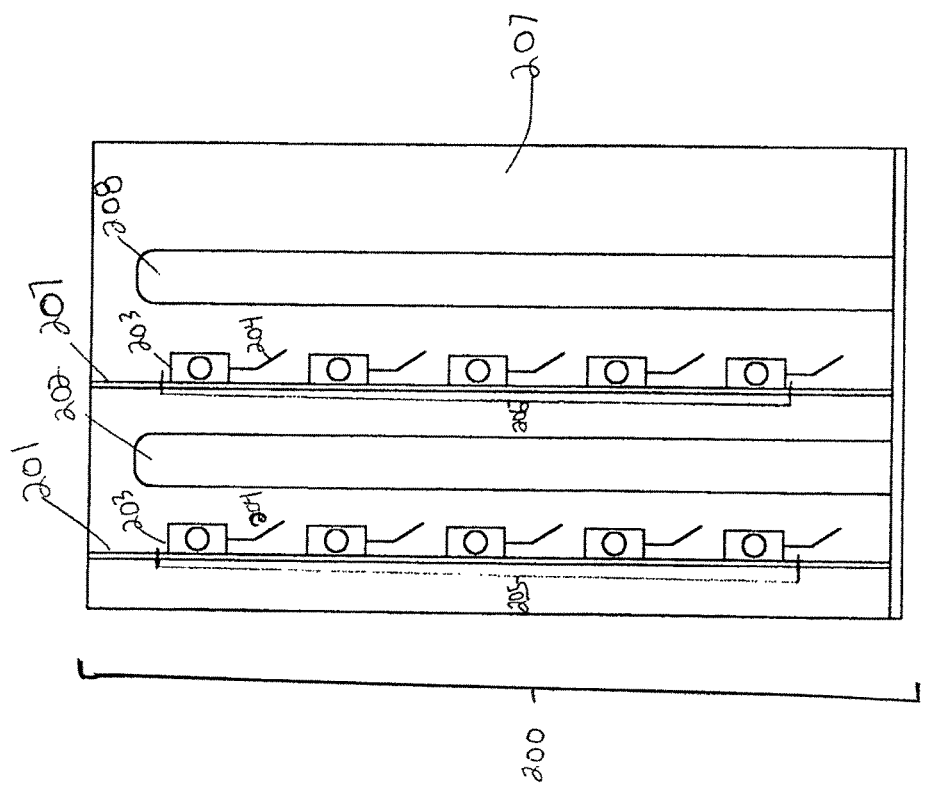
FIG. 2 depicts a vertical panel of an imaging device in accordance with the present invention.

FIG. 2 depicts an exemplary panel 200 of a TIP system in accordance with the present invention. Supporting the panel 200, is perimeter wall 207. Perimeter wall 207 can be flat, curved or angled in any fashion to accommodate the desired perimeter shape. Supported by the perimeter wall 207 are imaging arrays 205 and 206 and light sources 202 and 208. While this exemplary panel utilizes dual imaging arrays 205, 206 and light sources 202, 208, the panel may be configured in any fashion utilizing at least one imaging array. Light sources 202, 208 are optional, and depending on the type of imaging done, e.g., chemical, may be unnecessary. However, in the present embodiment, light sources 202 and 208 are taken to be standard fluorescent tubes. They could also be, for example, Wood's lamps. Imaging arrays 205 and 206 comprise a plurality of imaging devices 203. Imaging devices 203 may be a standard or digital camera, or any other type of device capable of capturing the desired information from the subject with the imaging system. Imaging devices 203 are controlled through cables 204. These cables may be used to remotely trigger a mechanical actuator or, as is contemplated herein, act as part of an electronic interface such as USB. Imaging arrays 205 and 206 are depicted herein as vertical arrays of 5 imaging devices 203. In practice, the array can vary greatly. For use in smaller examinations, e.g., the scalp, it is suggested that less imaging devices 203 would be required to generate a complete image.

Figure 3:
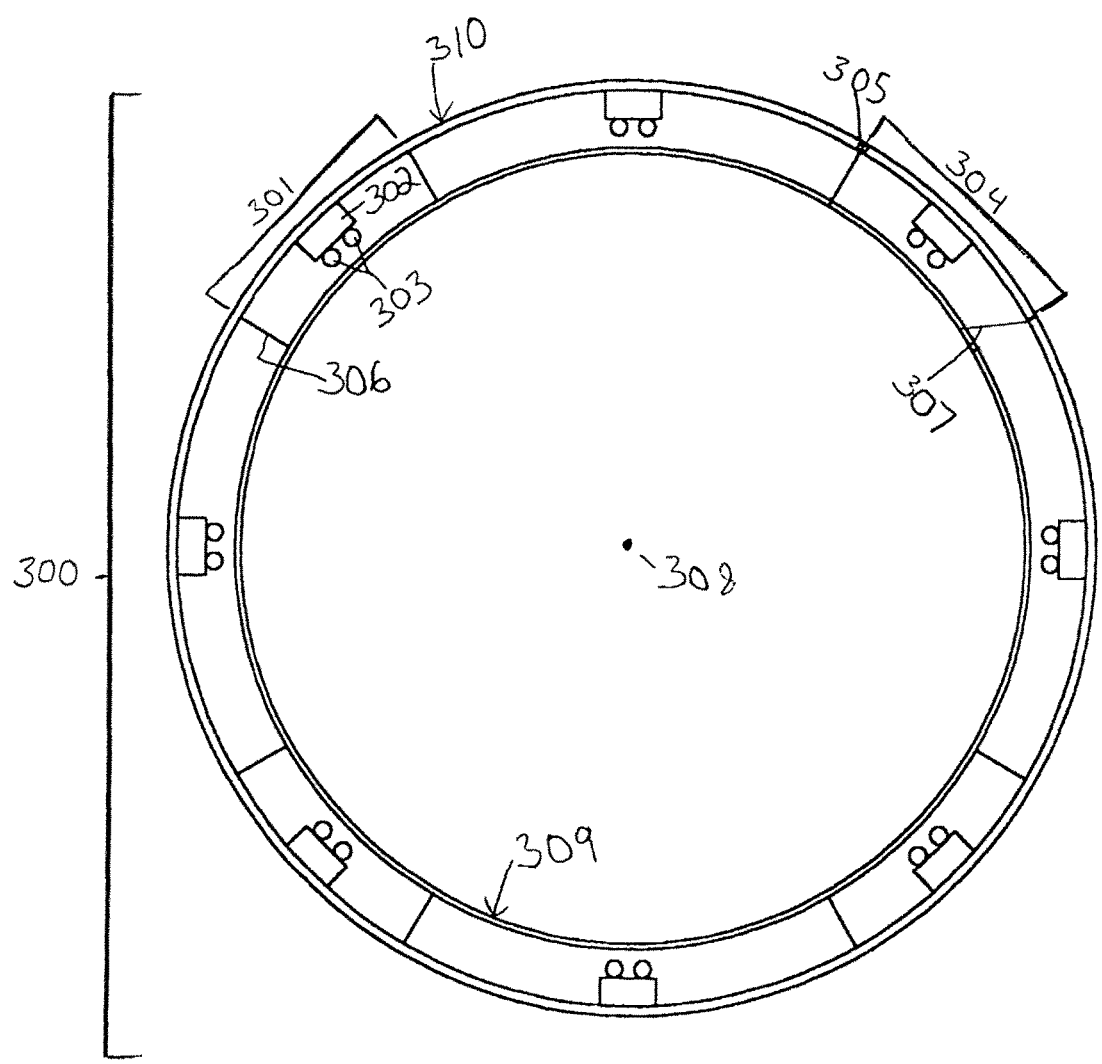
FIG. 3 depicts a horizontal cross section of an alternate embodiment of an imaging system in accordance with the present invention utilizing a circular periphery.

FIG. 3 depicts a horizontal cross section of an alternate embodiment of an imaging system 300 in accordance with the present invention utilizing a circular periphery. The system 300 may be sized in any fashion to accord with the application. For example, should the system be used to image an entire person, the system will be sized such that the person could easily stand at the center 308 of the device 300 with sufficient comfort. However, if the particular application is for the examination of something smaller, the scalp, for example, the device could be made smaller such that just a person's cranium would comfortably at center 308. The system 300 is comprised of several panels 309. In this particular embodiment, eight (8) panels are used. The panels are interconnected to form an enclosed structure. In this particular embodiment, a circle was constructed. The shape is arbitrary, however, the only requirement is that the panels are set up in mirrored pairs. Each panel 301 is comprised of an imager array 302, comprising a vertical array of imaging devices. The imaging devices could comprise standard or digital cameras, or other devices capable of capturing light, temperature or chemical information. In this embodiment, we assume the use of digital cameras operating in the conventional fashion. Thus, in order to optimize the performance of the cameras, light sources 303 are utilized. While fluorescent tubes are the preferred means, any type of illumination can be used. These light sources 303 can be always on, or, alternatively, only activated when the cameras are operating. Supporting the imager array 302 is the perimeter wall 310. The perimeter wall can be made of plywood, particleboard or any other structural material capable of supporting the structure. In front of the light sources 303 and imager array 302 is shield 309. Shield 309 protects the imager array 302 and light sources 303 from contact with the subject. Standard ⅛" obscured plexiglass can be used as shield 309, and furthermore, a shield with variable transmittance is contemplated. In between the plurality of panels 301, there are dividers 306. Dividers 306 function to provide stability for shield 309, and also, when made opaque, reduce light interference between adjacent imager arrays 302. To effect access and egress, panel 304 functions as a doorway. By rotating on a double-hinge hinge 305 and clearing angled divider 307, panel 304 swings outward, thus allowing access to the interior of system 300. A system 300 is also contemplated without doorway 304 that can be used for examining small objects, such as the scalp or hands, for example.

Figure 4:
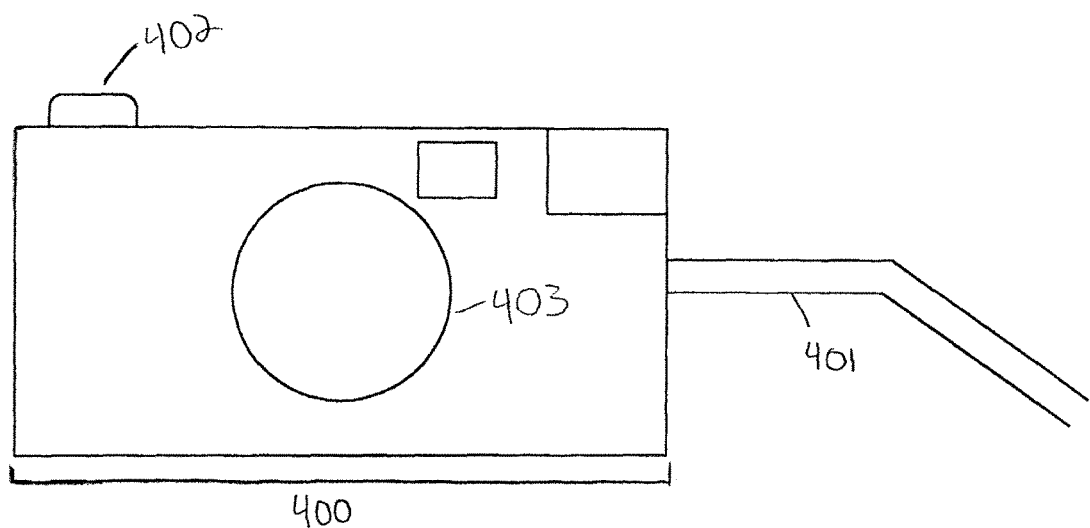
FIG. 4 depicts an exemplary imaging device, e.g., camera, and actuation means.

FIG. 4 depicts an exemplary imaging device 400 for use with the present invention. In practice, the imaging device 400 may be a standard or digital camera, or any other type of device capable of capturing the desired information from the subject with the imaging system. For example, devices capable of recording infrared or chemical information could be used. The present embodiment, however, contemplates the use of a digital camera as exemplified by the current figure. Such a device would comprise lens 403, mechanical actuator 402 and control cable 401. Preferably, cable 401 is used to electronically control, and further, download digital image information from imaging device 400. As is contemplated herein, the electronic control could be USB. Alternatively, control cable 401 could be used to trigger mechanical actuator 402. Although the present figure describes a specific imaging device, it should be understood that a wide variety of data collection devices could be employed without departing from the scope of the present invention.

Figure 5:
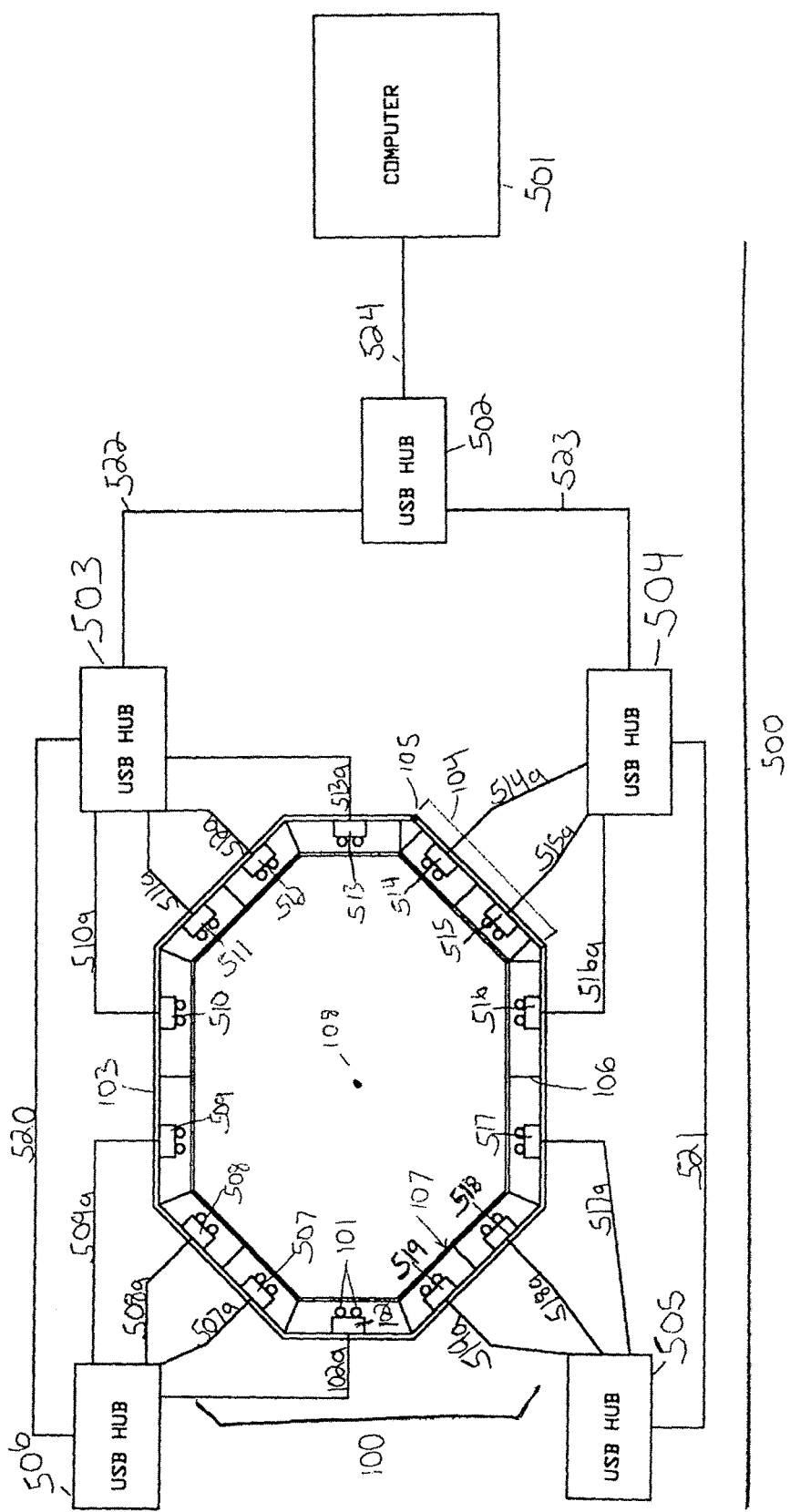
FIG. 5 is a schematic of a complete imaging system in accordance with the present invention.

FIG. 5 depicts a schematic of a complete image processing system 500 in accordance with the present invention. As discussed above in FIG. 1, imaging system 100 may be sized in any fashion to accord with the application. For example, should the system be used to image an entire person, the system will be sized such that the person could easily stand at the center 108 of the device 100 with sufficient comfort. However, if the particular application is for the examination of something smaller, the scalp, for example, the device could be made smaller such that just a person's cranium would fit comfortably at center 108. The system 100 is comprised of several panels 109. In this particular embodiment, fourteen (14) panels are used. The panels are interconnected to form an enclosed structure. In this particular embodiment, an 8-sided polygon was chosen. The shape is arbitrary, however, the only requirement is that the panels are set up in mirrored pairs. Each panel 109 is comprised of an imager array 102, comprising a vertical array of imaging devices. Imaging arrays 507 through 519 can be identical to imager array 102, or may vary in the information they garner in accord with the desired application. The present embodiment, however, contemplates identical imaging devices. The imaging devices could comprise standard or digital cameras, or other devices capable of capturing light, temperature or chemical information. In this embodiment, we assume the use of digital cameras operating in the conventional fashion. Thus, in order to optimize the performance of the cameras, light sources 101 are utilized. Each imaging array may utilize a light source 101 to enhance imaging ability. Furthermore, each of said light sources could have varying characteristics to accord with the application. While fluorescent tubes are the preferred means, any type of illumination can be used. These light sources 101 can be always on, or, alternatively, only activated when the cameras are operating. Supporting the imager array 102 is the perimeter wall 103. The perimeter wall can be made of plywood, particle board or any other structural material capable of supporting the structure. In front of the light sources 101 and imager arrays 102 and 507-519 is shield 107. Shield 107 protects the imager arrays 102 and 507 through 519 and light sources 101 from contact with the subject. Standard 1/8" obscured plexiglass can be used as shield 107, and furthermore, a shield with variable transmittance is contemplated. In between the plurality of panels 109, there are dividers 106. Dividers 106 function to provide stability for shield 107, and also, when made opaque, reduce light interference between adjacent imager arrays 102 and 507 through 519. To effect access and egress, panels 104 function as a doorway. By rotating on hinge 105, panels 104 swing outward, thus allowing access to the interior of system 100. A system 100 is also contemplated without doorway 104 that can be used for examining small objects, such as the scalp or hands, for example. In order to effect the processing of the multiple images garnered from the plurality of imaging arrays, the imager arrays 102 and 507 through 519 are networked to a single computer 501. The present embodiment contemplates the use of USB to network the arrays 102 and 507 through 519. The imaging devices of arrays 102, 507, 508 and 509 are connected to USB hub 506 via interface cabling 102a, 507a, 508a and 509a, respectively. The imaging devices of arrays 517, 518 and 519 are connected to USB hub 505 via interface cabling 517a, 518a and 519a, respectively. The imaging devices of arrays 514, 515 and 516 connected to USB hub 504 via interface cabling 514a, 515a and 516a, respectively. The imaging devices of arrays 510, 511, 512 and 513 are connected to USB hub 503 via interface cabling 510a, 511a, 512a and 513a, respectively. Hub 506 is connected with hub 503 via cable 520. Hub 505 is connected with hub 504 via cable 521. Hubs 503 and 504 are then connected to hub 502 via cables 522 and 523, respectively. Finally, hub 502, which has the totality of imaging devices of imaging arrays 102 and 507 through 519 connected thereto, is connected to computer 501 via cable 524. The computer 501 is used to process the individual images garnered from each imaging device of each imaging array 102 and 507 through 519 to create a non-occluded image of the subject within system 100, and preferably, at center 108. It should be noted that the arrangement of hubs 506, 505, 504, 503 and 502 and the concomitant cabling presented heretofore is merely exemplary, and anyone with skill in the art will recognize the myriad ways of interconnecting the imaging devices of imaging arrays 102 and 507 through 519 to computer 501.

While the present invention has been described with reference to one or more preferred embodiments, which embodiments have been set forth in considerable detail for the purposes of making a complete disclosure of the invention, such embodiments are merely exemplary and are not intended to be limiting or represent an exhaustive enumeration of all aspects of the invention. The scope of the invention, therefore, shall be defined solely by the following claims. Further, it will be apparent to those of skill in the art that numerous changes may be made in such details without departing from the spirit and the principles of the invention.

What is claimed is:

1. A method comprising the following steps:
   introducing into an enclosure a person or portion thereof for imaging the person or portion thereof with an array of imaging devices located and affixed about a perimeter of the enclosure;
   locating the person or portion thereof at a specified position for imaging within the enclosure, wherein the specified imaging position defines a centerline, the array of imaging devices includes a plurality of imaging devices located on opposite sides of the centerline relative to each other, a plurality of imaging devices located on one side of the centerline are vertically and laterally spaced relative to each other, a plurality of imaging devices located on an opposite side of the centerline are vertically and laterally spaced relative to each other, and each imaging device is located a fixed distance relative to the specified imaging position;
   illuminating the person or portion thereof located at the specified imaging position with a plurality of light sources that are spaced relative to each other amongst the plurality of imaging devices;
   generating refraction and reflectance light by illuminating the person or portion thereof with the plurality of light sources;
   substantially simultaneously generating, with each of a plurality of said imaging devices that are vertically and laterally spaced relative to each other, an individual image of the illuminated person or portion thereof located at the specified imaging position, wherein each said imaging device defines respective coordinates and said respective fixed distance relative to the specified imaging position, and defines a respective focal length and resolution information, allowing precise measurement of imaged features of the person or portion thereof located at the specified imaging position; and
   using images generated during the substantially simultaneously generating step to precisely measure one or more imaged features of the person or portion thereof located at the specified imaging position.

2. A method as defined in claim 1, further comprising generating an individual image of the illuminated person or portion thereof with each of a plurality of said plurality of imaging devices that are vertically spaced from each other and said plurality of imaging devices that are laterally spaced relative to each other located on opposite sides of the centerline relative to each other.

3. A method as defined in claim 1, wherein the illuminating step includes illuminating the person or portion thereof with at least two of said light sources located lateral to at least two of said imaging devices.

4. A method as defined in claim 1, wherein the illuminating step includes illuminating the person or portion thereof with at least two of said light sources positioned symmetrically relative to the centerline.

5. A method as defined in claim 1, wherein:
   the array of imaging devices includes a first imaging array spaced a fixed distance away from and relative to the specified imaging position to a side of the enclosure, wherein the first imaging array includes a first plurality of said imaging devices vertically spaced relative to each other; and
   a second imaging array spaced a fixed distance away from and relative to the specified imaging position, and laterally spaced adjacent to the first imaging array on an opposite side of the centerline of the specified imaging position relative to the first imaging array, wherein the second imaging array includes a second plurality of said imaging devices vertically spaced relative to each other.

6. A method as defined in claim 5, wherein:
the array of imaging devices includes a third imaging array spaced a fixed distance away from and relative to the specified imaging position, and laterally spaced relative to the first imaging array on an opposite side of the first imaging array relative to the second imaging array, wherein the third imaging array includes a third plurality of said imaging devices vertically spaced relative to each other; and
a fourth imaging array spaced a fixed distance away from and relative to the specified imaging position, and laterally spaced relative to the second imaging array on an opposite side of the second imaging array relative to the first imaging array, wherein the fourth imaging array includes a fourth plurality of said imaging devices vertically spaced relative to each other.

7. A method as defined in claim 6, wherein the plurality of light sources are positioned symmetrically about the centerline and includes a first light source located lateral to the first imaging array, a second light source located between the first and second imaging array, a third light source located between the third and fourth imaging arrays and symmetrically about the centerline to the second light source, and a fourth light source located opposite the first light source and lateral to the fourth imaging array.

8. A method as defined in claim 1, further comprising the step of enclosing the person or portion thereof with panels throughout a radius selected from one or more of: 360 degrees about a vertical axis or 360 degrees about a horizontal axis.

9. A method as defined in claim 8, wherein the panels include at least one of said imaging devices.

10. A method as defined in claim 1, further comprising the steps of capturing with all of the plurality of imaging devices one or more of: (i) light in the humanly perceivable light spectrum; (ii) infrared emissions; (iii) electrical emissions; (iv) magnetic emissions; (v) chemical emissions; or (vi) temperature emissions.

11. A method as defined in claim 1, further comprising the steps of producing with the plurality of light sources an amount of illumination for the plurality of imaging devices to function in one or more of: (i) light in the humanly perceivable light spectrum; (ii) infrared emissions; (iii) electrical emissions; (iv) magnetic emissions; (v) chemical emissions; or (vi) temperature emissions.

12. A method as defined in claim 8, wherein the panels include a material capable of allowing an amount of illumination to pass through the panels and the method includes illuminating the person or portion thereof with the light sources through the panels.

13. A method as defined in claim 1, further comprising the steps of scanning the illuminated person or portion thereof synchronously and asynchronously from a physically dispersed matrix of cameras and multiply angled multiply-angled lighting sources.

14. A method as defined in claim 1, wherein the person or portion thereof includes a surface of the person's skin.

15. A method as defined in claim 1, wherein the substantially simultaneously generating step includes photographing the illuminated person or portion thereof with each of at least a plurality of the imaging devices of the array.

16. A method as defined in claim 1, further comprising repeating the locating, illuminating, generating refraction and reflectance light, and substantially simultaneously generating steps with the person or portion thereof at a second specified imaging position.

17. A method as defined in claim 1, further comprising performing said substantially simultaneously generating step at a first point in time, generating at least one first measurement of said one or more imaged features, repeating the locating, illuminating, generating refraction and reflectance light, and substantially simultaneously generating steps at a later point in time, using images generated at the second point of time to precisely measure said one or more imaged features, generating at least one second measurement of said one or more imaged features at said later point in time, comparing said at least one first measurement and said at least one second measurement, and determining any change of said one or more imaged features between the first point in time and the later point in time based on said at least one first measurement of said one or more imaged features at said first point in time and said at least one second measurement of said one or more imaged features at said later point in time.

18. A method as defined in claim 1, wherein the enclosure encloses the person throughout a radius selected from one or more of: 360 degrees about a vertical axis or 360 degrees about a horizontal axis.

19. A method as defined in claim 1, wherein the one or more imaged features includes one or more maladies of the skin.

20. A method as defined in claim 19, wherein the one or more maladies of the skin is one or more of a mole, a beauty mark, skin cancer, skin disease or a wound.

21. A method as defined in claim 17, wherein the one or more imaged features includes one or more maladies of the skin.

22. A method as defined in claim 21, wherein the one or more maladies of the skin is one or more of a mole, a beauty mark, skin cancer, skin disease or a wound.

23. A method as defined in claim 1, wherein the substantially simultaneously generating step includes transferring image information to a computer for processing and aggregation.

24. A method as defined in claim 1, further comprising using a measurement of the one or more imaged features to screen for one or more of melanoma, skin cancer or other maladies of the skin.

25. A method as defined in claim 24, wherein the one or more imaged features are a potentially cancerous lesion.

26. A method as defined in claim 25, further comprising evaluating change over time of the one or more imaged features and detecting new lesions by repeatedly imaging the same person or portion thereof over time and analyzing images obtained thereby in relation to one another.

27. A method as defined in claim 1, wherein the substantially simultaneously generating step includes image data acquisition and collection.

28. A method as defined in claim 27, wherein the substantially simultaneously generating step further includes, with respect to said image data, data aggregation, data dissemination, data manipulation and data viewing.

29. A method as defined in claim 1, wherein, during the substantially simultaneously generating step, the person or portion thereof located at the specified imaging position is in a static position.

30. A method as defined in claim 1, further comprising transmitting said individual image from a respective imaging device to a computer configured to aggregate, manipulate and disseminate transmitted images into a visually discernable format.

31. A method as defined in claim 30, further comprising displaying said transmitted images in 2D format or processing the images into 3D renderings.

32. A method as defined in claim 1, further comprising combining a plurality of said individual images into a continuous image.

33. A method as defined in claim 1, wherein the array includes a plurality of vertical arrays laterally spaced relative to each other about the perimeter.

34. A method as defined in claim 33, wherein each vertical array is supported on a perimeter wall of the enclosure.

35. A method as defined in claim 1, further comprising introducing the person or portion thereof through a doorway of the enclosure and into the enclosure.

36. A method as defined in claim 1, wherein each of a plurality of the imaging devices is a digital camera comprising a lens, an actuator and a control cable, and the substantially simultaneously generating step includes actuating each actuator via a respective control cable.

37. A method as defined in claim 1, wherein the light sources are separate from, and spaced relative to, the imaging devices.

38. A method as defined in claim 1, wherein the perimeter defines a horizontal perimeter about the specified imaging position, and the plurality of imaging devices are affixed about the horizontal perimeter.

* * * * *